(12) United States Patent
Kraz et al.

(10) Patent No.: US 7,539,002 B1
(45) Date of Patent: May 26, 2009

(54) SELF-DISENGAGING WEARABLE GROUNDING DEVICE

(75) Inventors: Vladimir Kraz, Santa Cruz, CA (US); Kirk Alan Martin, Aptos, CA (US); Fatjon Gurga, San Jose, CA (US); Yelena Kraz, Santa Cruz, CA (US); Elis Pogace, San Jose, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 515 days.

(21) Appl. No.: 11/497,160

(22) Filed: Jul. 31, 2006

Related U.S. Application Data

(63) Continuation-in-part of application No. 10/434,765, filed on May 8, 2003, now Pat. No. 7,085,120.

(60) Provisional application No. 60/460,356, filed on Apr. 3, 2003.

(51) Int. Cl.
*H02H 3/00* (2006.01)
*H02H 1/00* (2006.01)

(52) U.S. Cl. ................................................. 361/220

(58) Field of Classification Search .................. 361/220
See application file for complete search history.

(56) References Cited

U.S. PATENT DOCUMENTS

| | | | | |
|---|---|---|---|---|
| 4,745,519 A | * | 5/1988 | Breidegam | 361/220 |
| 4,859,992 A | * | 8/1989 | Hoigaard | 340/649 |
| 5,004,425 A | | 4/1991 | Hee | |
| 5,051,732 A | * | 9/1991 | Robitaille | 340/650 |
| 5,057,965 A | * | 10/1991 | Wilson | 361/212 |
| 5,408,186 A | * | 4/1995 | Bakhoum | 324/509 |
| 5,510,771 A | * | 4/1996 | Marshall | 340/573.4 |
| 5,952,931 A | * | 9/1999 | Chotichanon et al. | 340/649 |
| 6,035,260 A | * | 3/2000 | Pohribnij et al. | 702/58 |
| 6,205,408 B1 | * | 3/2001 | Jubin et al. | 702/182 |
| 6,930,612 B1 | * | 8/2005 | Kraz et al. | 340/649 |
| 7,085,120 B2 | | 8/2006 | Kraz | |
| 7,193,837 B1 | * | 3/2007 | Epstein | 361/220 |
| 2006/0114087 A1 | | 6/2006 | Deng | |

FOREIGN PATENT DOCUMENTS

KR  20020080766 A  10/2002

* cited by examiner

*Primary Examiner*—Ronald W Leja
(74) *Attorney, Agent, or Firm*—Johannes P. M. Kusters

(57) ABSTRACT

The invention is a grounding device that grounds the wearer when the wearer is in a designated area and automatically disengages when the wearer leaves the designated area. The device may include a magnetic wriststrap connector that disengagably connects to a wriststrap terminal (or a wriststrap monitor when the terminal is integrated into the monitor). The wriststrap connector may provide an indication to the monitor of the proper mating of the connector and the terminal.

28 Claims, 26 Drawing Sheets

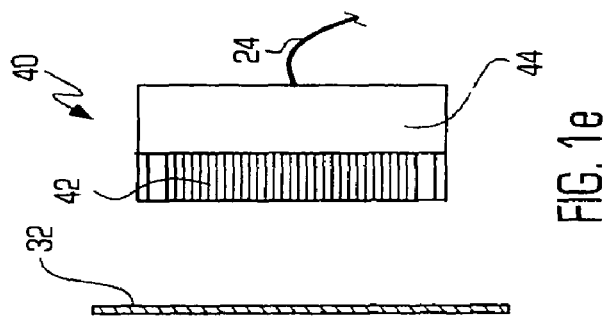
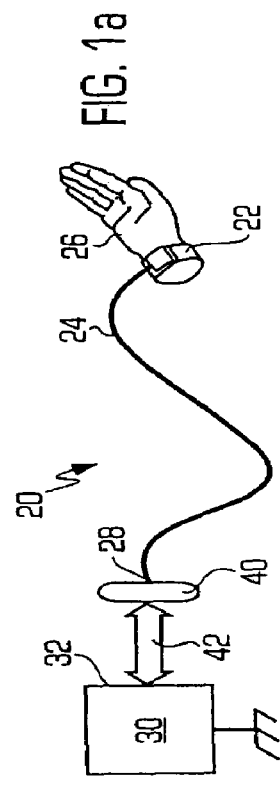
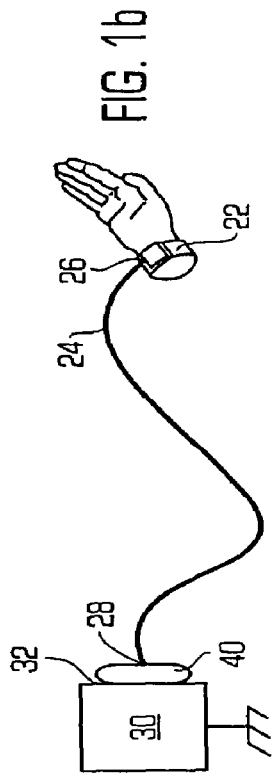
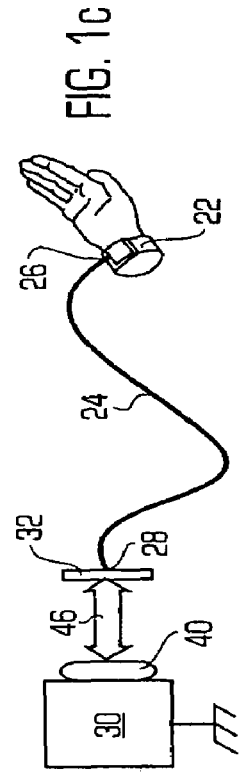
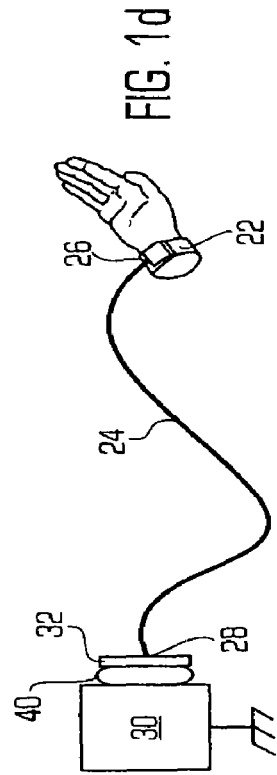

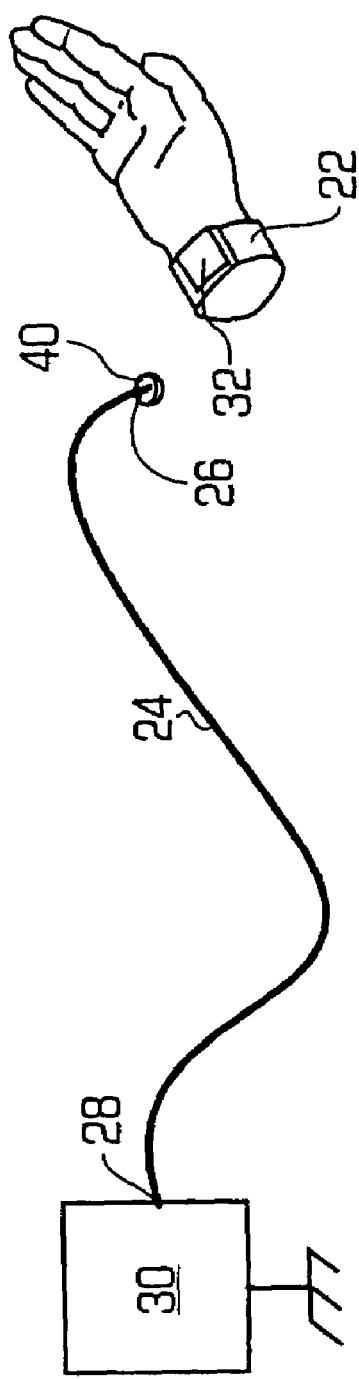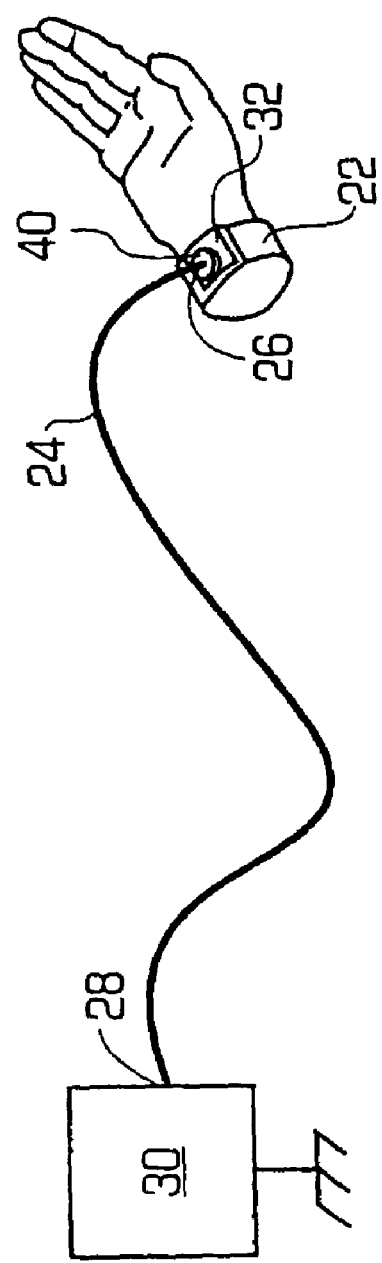

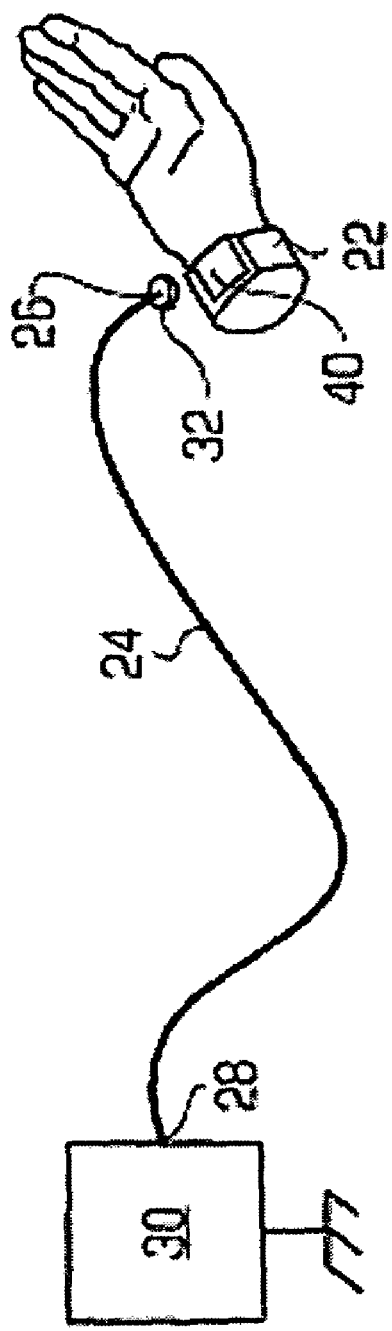
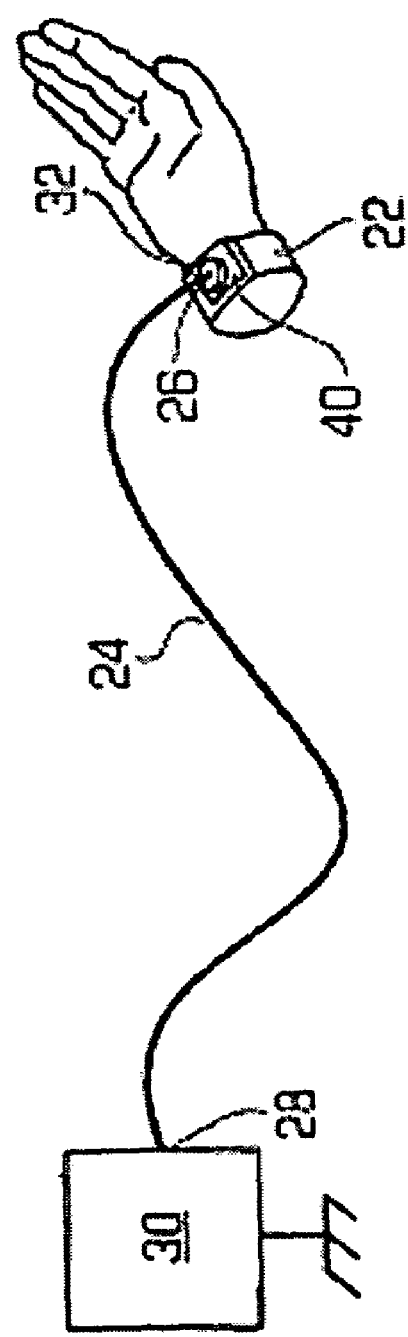

CORD UNWINDS AND IS HELD UNWOUND BY RATCHET

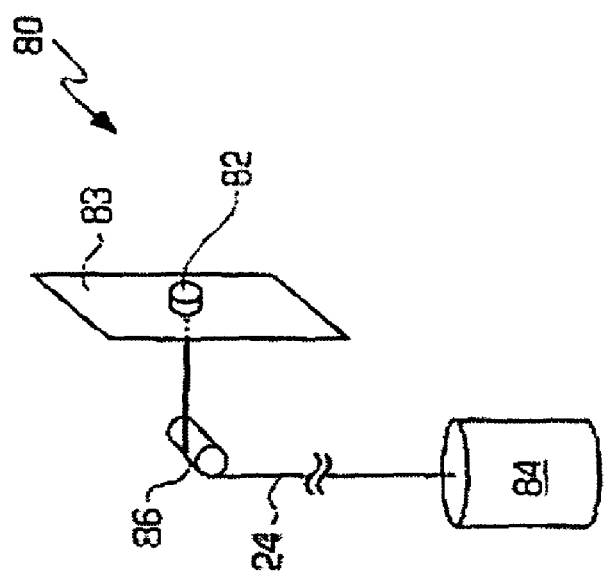
FIG. 7
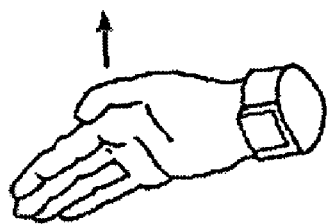
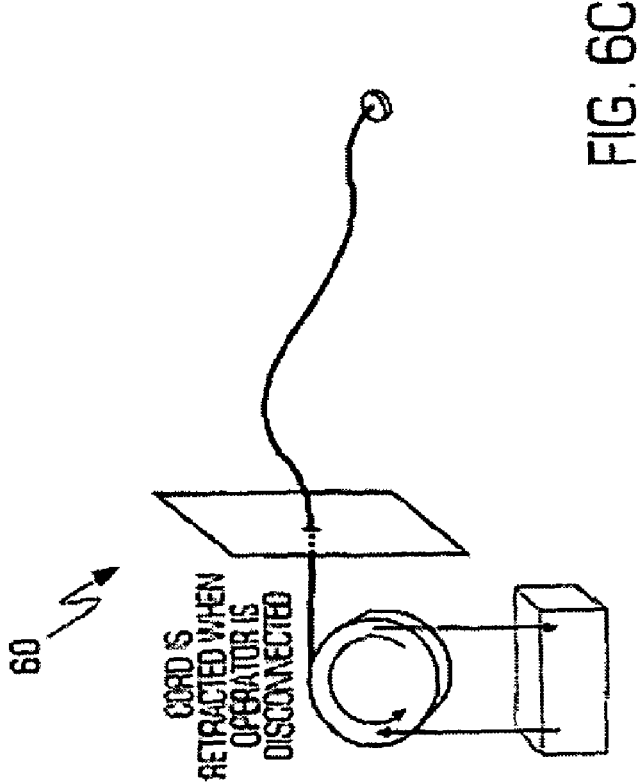
FIG. 6C

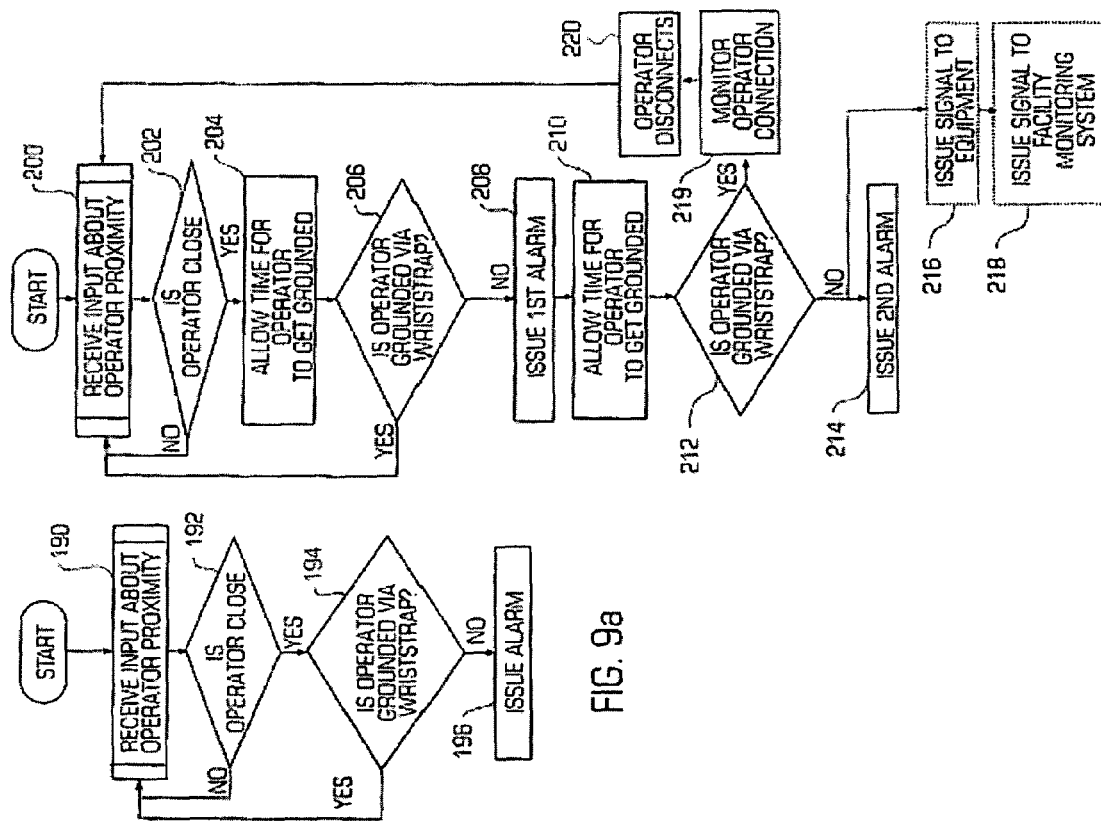

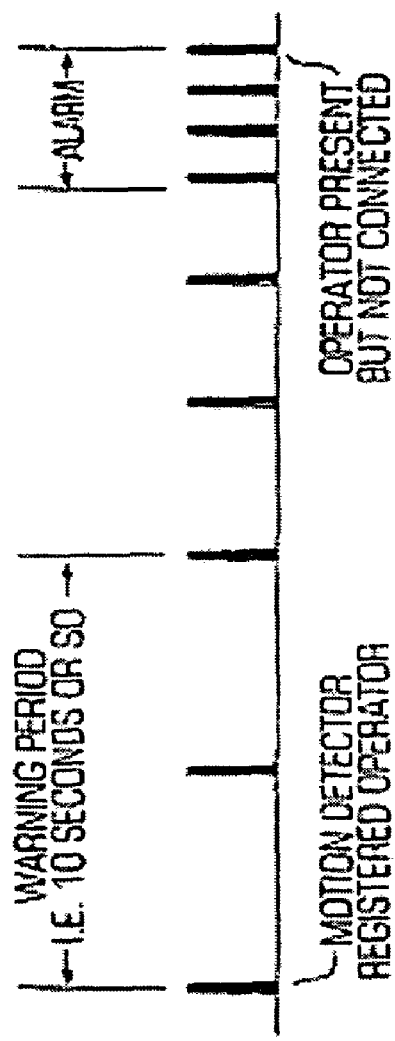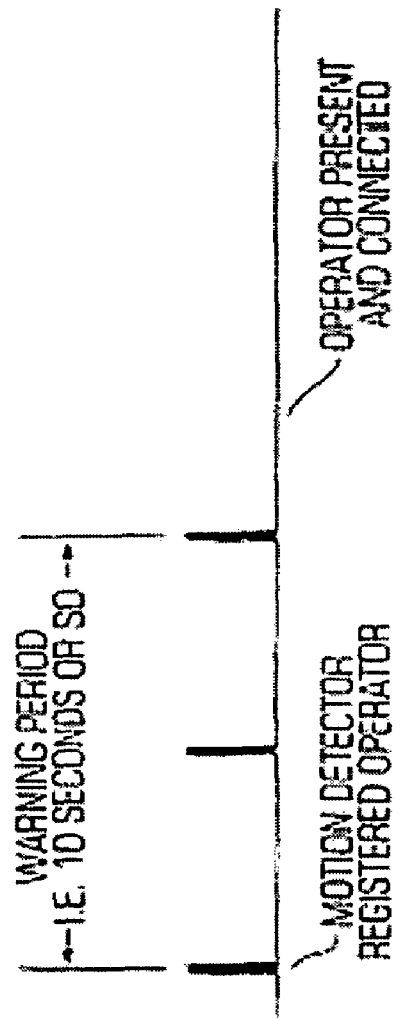

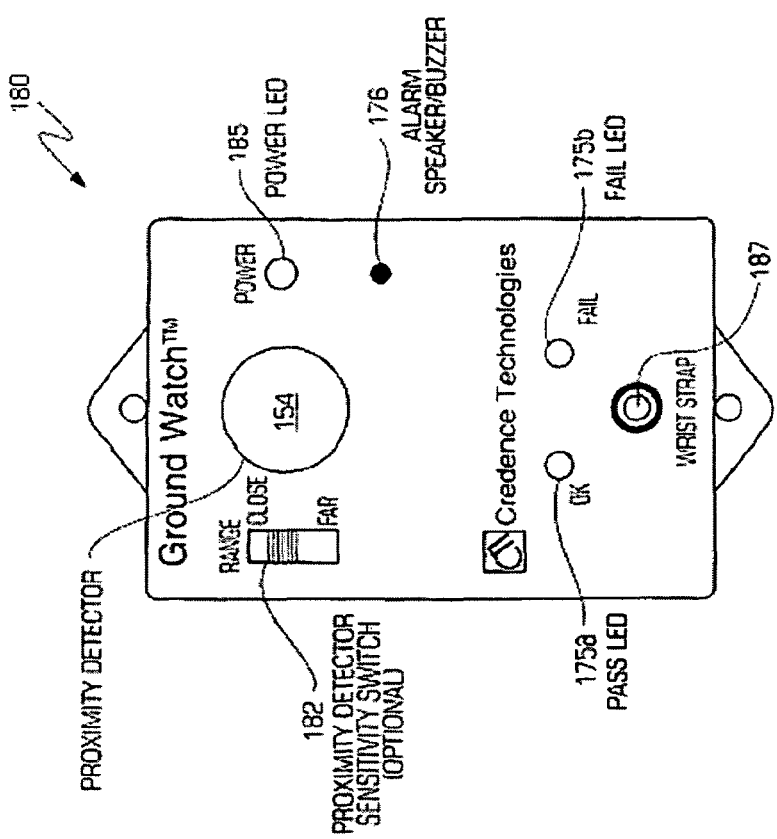
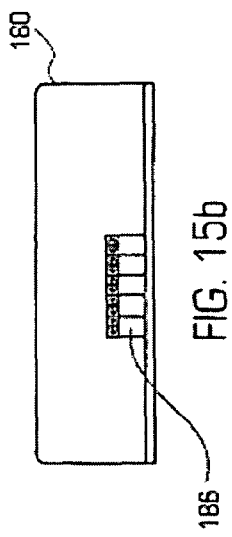
FIG. 15a
FIG. 15b

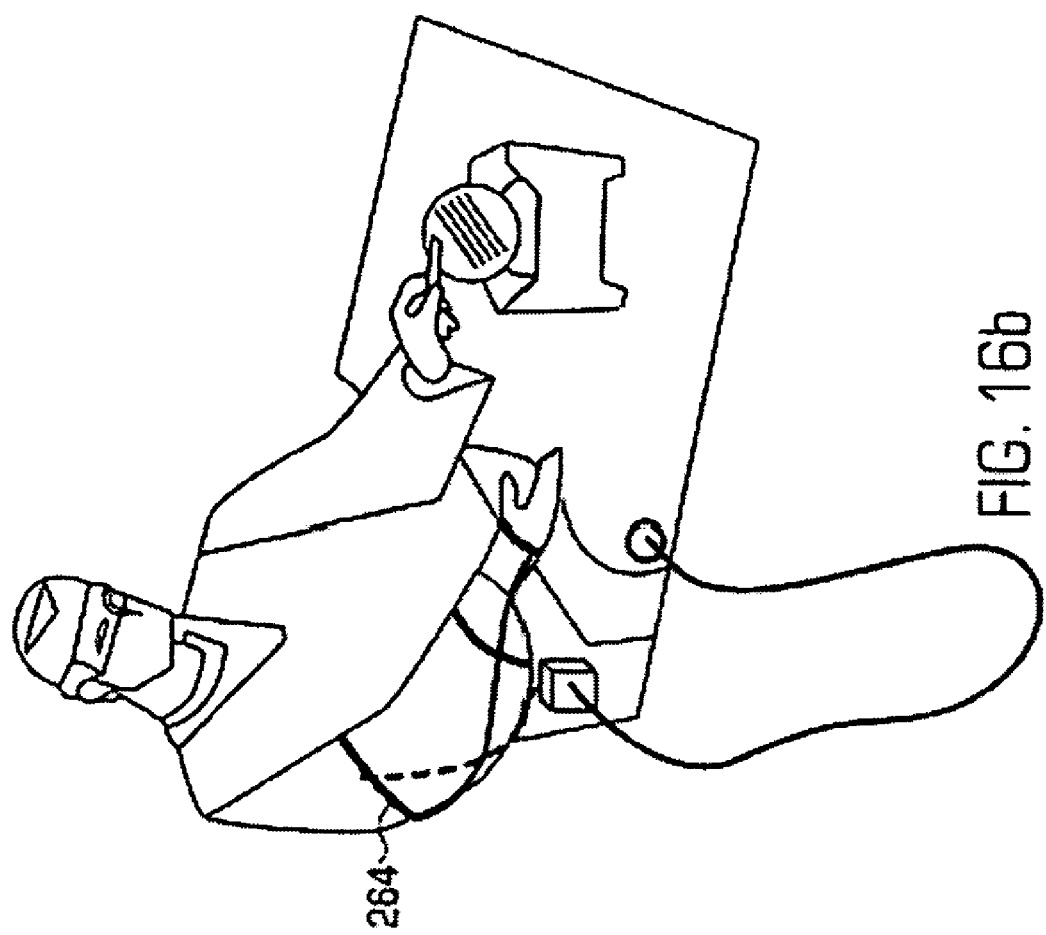
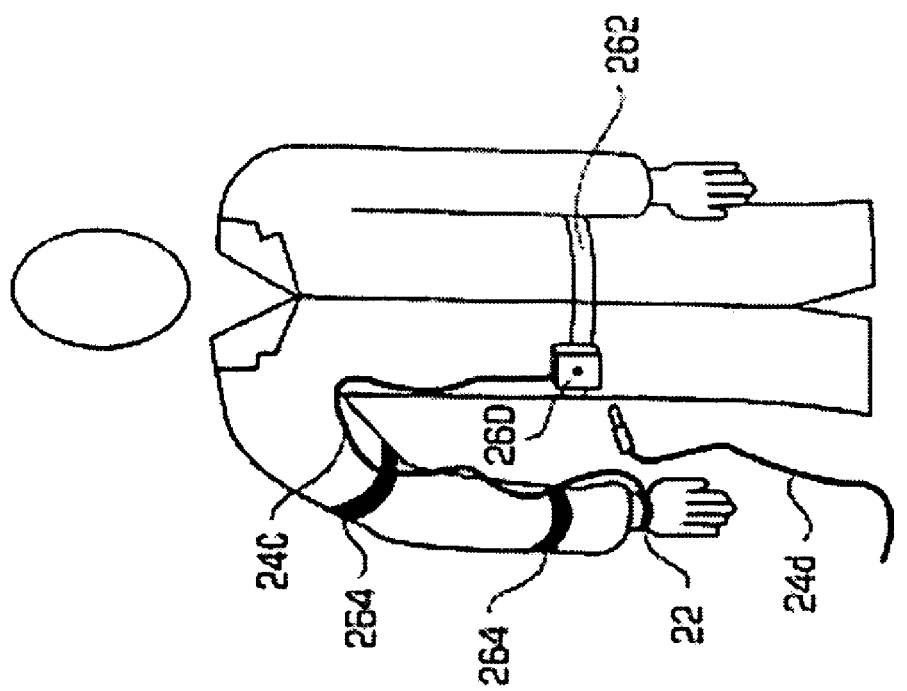
FIG. 16b
FIG. 16a

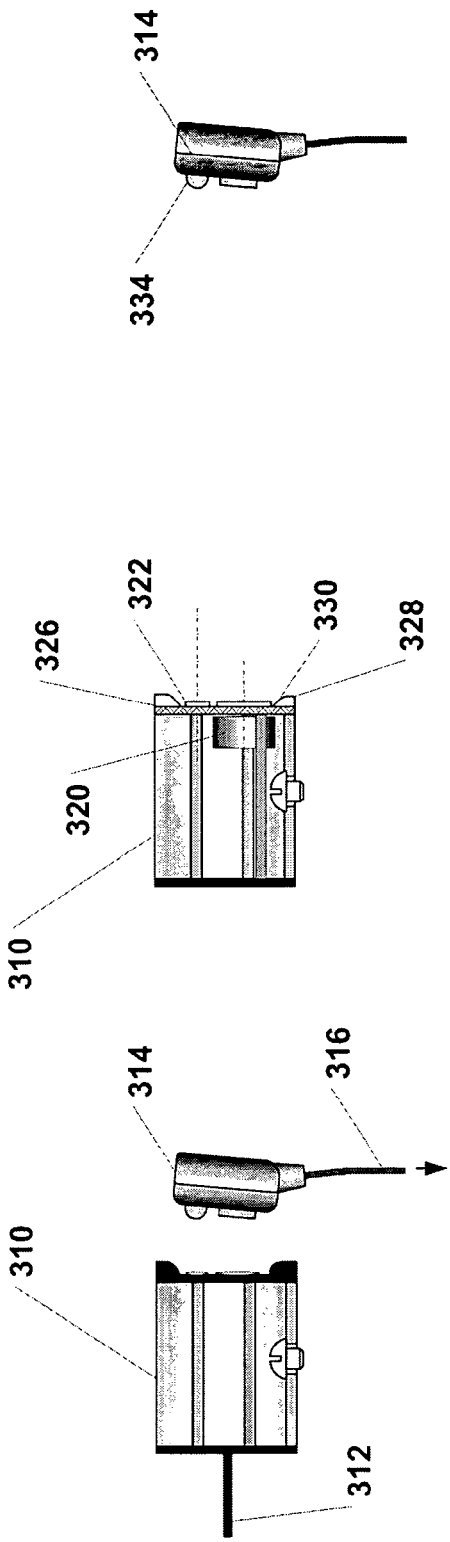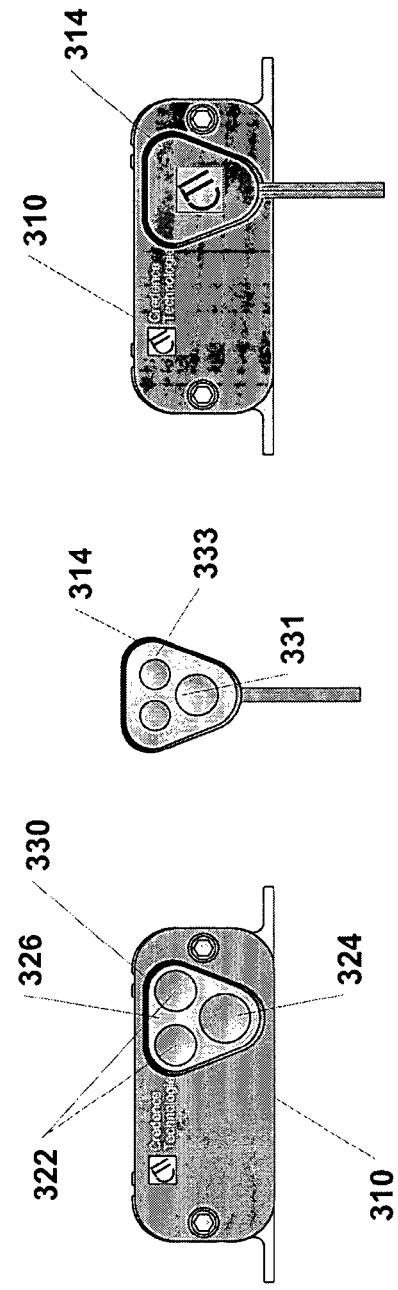

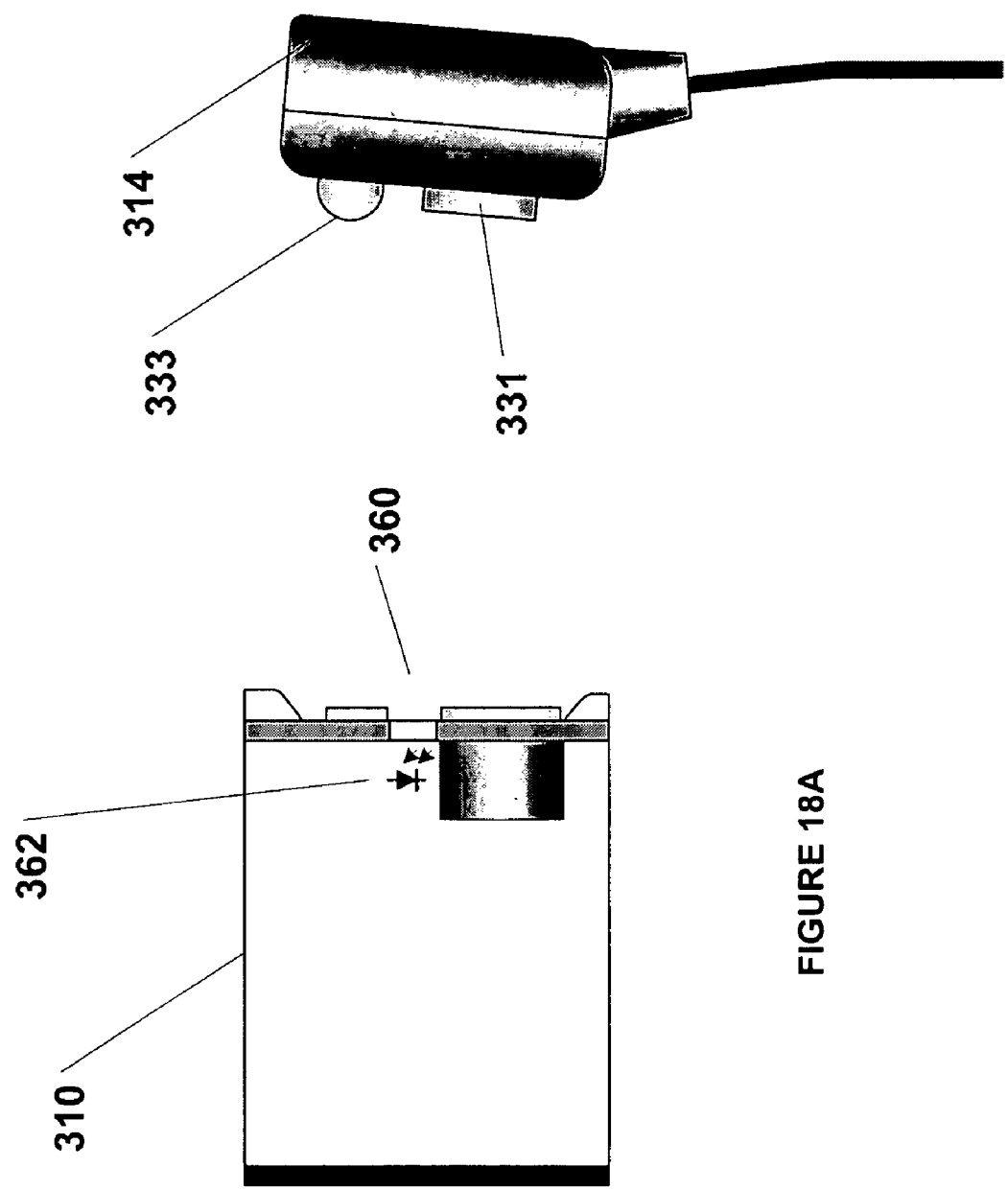

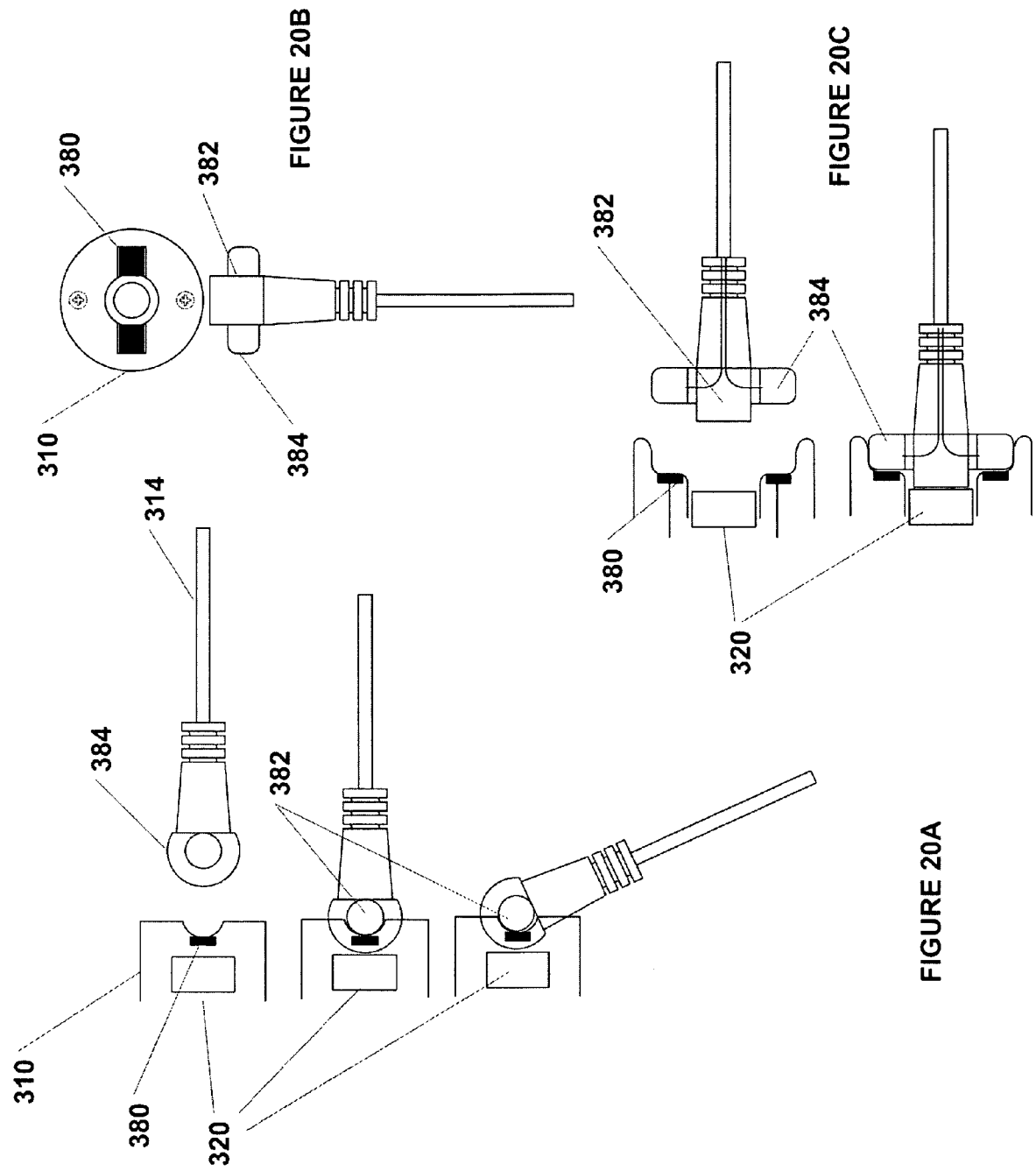

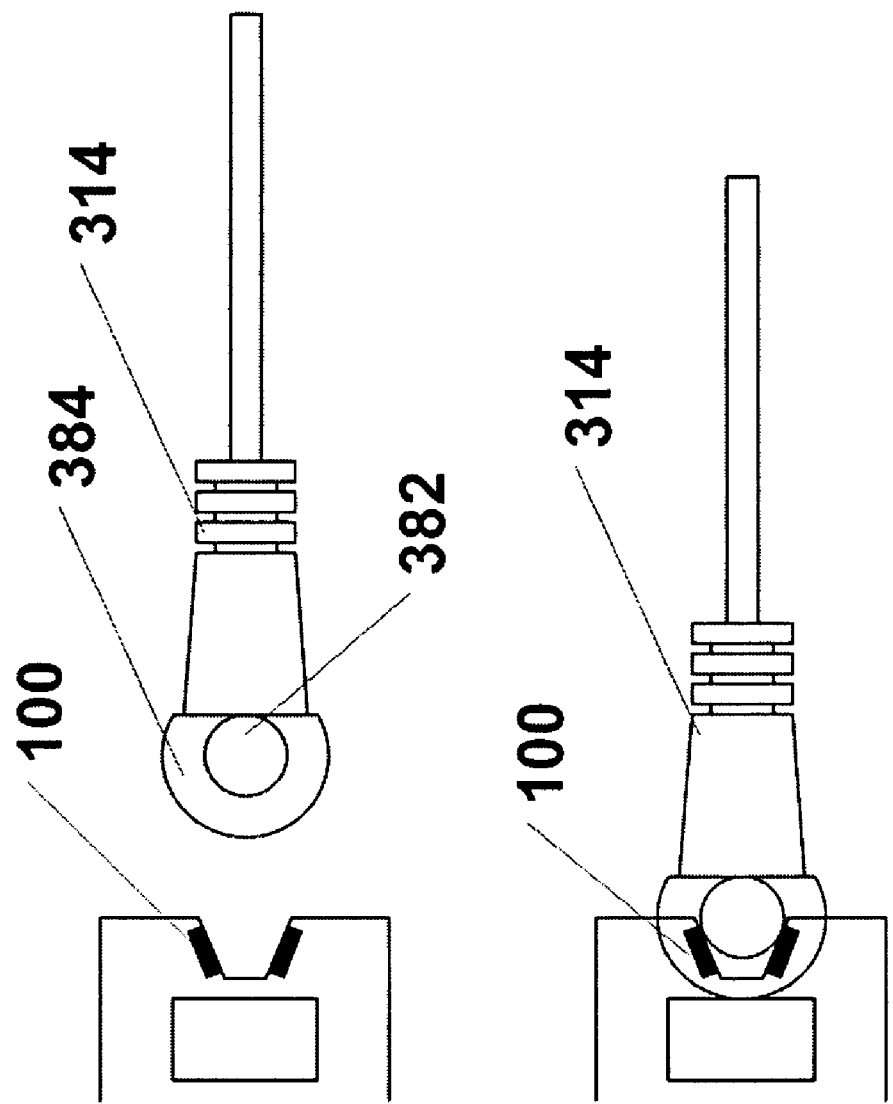

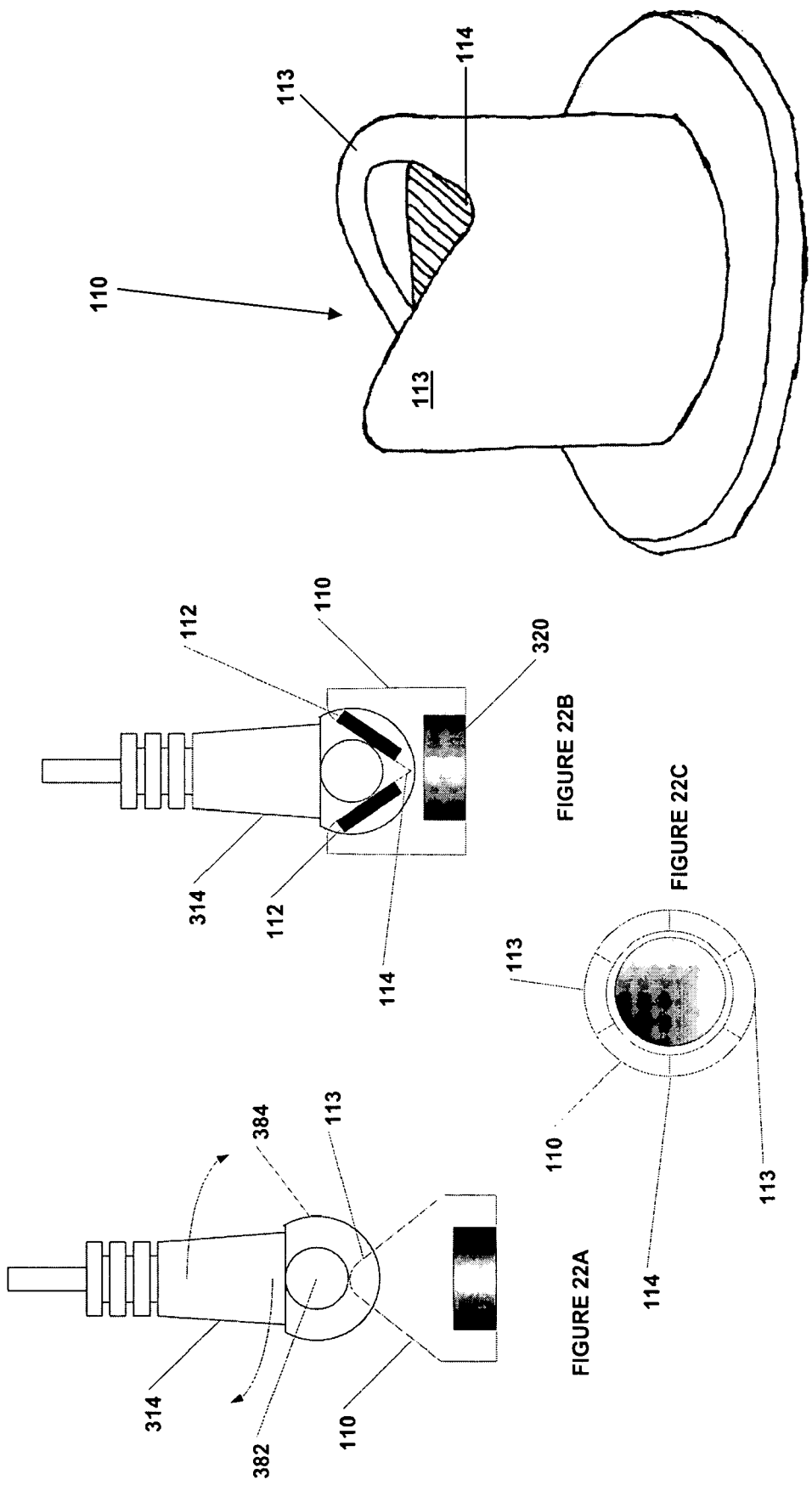

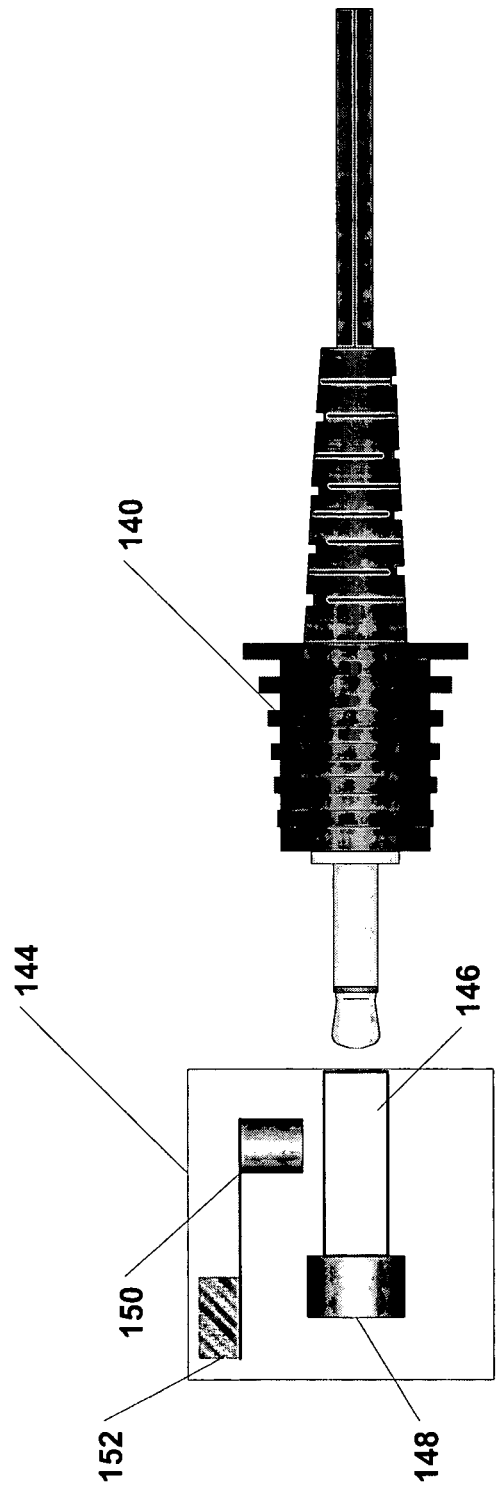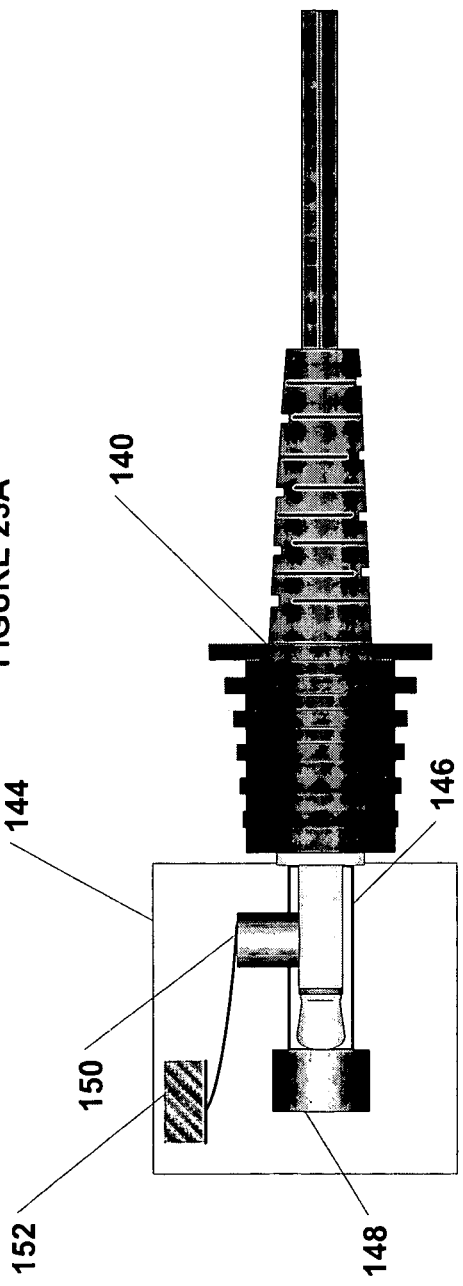
FIGURE 23A
FIGURE 23B

SELF-DISENGAGING WEARABLE GROUNDING DEVICE

PRIORITY CLAIMS/RELATED APPLICATION

This application is a continuation in part of and claims priority under 35 USC 120 to U.S. patent application Ser. No. 10/434,765 entitled "A SELF-DISENGAGING WEARABLE GROUNDING DEVICE" filed on May 8, 2003 now U.S. Pat. No. 7,085,120 which in turn claims priority to and claims the benefit under 35 U.S.C. § 119(e) of U.S. Provisional Application No. 60/460,356 filed on Apr. 3, 2003, both of which are incorporated herein by reference in its entirety.

FIELD OF THE INVENTION

The invention relates generally to a device, system, and method for grounding a user to prevent electrostatic discharge and in particular to a device, system, and method for a self-disengaging grounding device.

BACKGROUND OF THE INVENTION

It is well known that when operating equipment or a component that is sensitive to electrostatic discharge, operators must be grounded to prevent electrostatic damage to the sensitive equipment/component. Guidelines such as ANSI/ESDA S.20.20 standards (available at www.esda.org) provide requirements for operators to be grounded. These guidelines are typically met by requiring each operator to wear a wristband that is electrically connected to a grounding jack. Although the grounded wristband method seems like a sound solution in theory, it has proven to be highly unreliable in practice. Many operators do not follow the manufacturing procedure that requires them to wear the grounded wristbands because connecting the wristbands to the grounding jack is an inconvenient process, the wire that connects the wristband to the grounding jack interferes with movement, or because the operators forget to put them on. Sometimes, an operator mistakenly believes that he is grounded after putting on a wristband when in fact, the wristband is not securely connected to the grounding jack. For example, the wristband is sometimes worn over the operator's sleeve, making no direct connection to the operator. Due to the low reliability of the current wristband-based grounding system, many expensive manufacturing equipment continue to be damaged or destroyed by electrostatic discharge.

As mentioned above, one of the reasons operators fail to be properly grounded is because the process of connecting the wristband to the grounding jack is cumbersome, complicated, and/or inconvenient. Since operators are required to connect the wristband to the grounding jack every time they approach the sensitive equipment/component, and to disconnect the wristband every time they move away from the equipment/component, they often have to connect and disconnect their wristband numerous times in one day. Thus, any process but a very simple and quick connection/disconnection process becomes burdensome.

It is just as important for the operator to disconnect himself when leaving the designated area as for him to connect himself upon entering the designated area. If an operator leaves the equipment without disconnecting the wristband from the grounding jack, the connection wire may get stretched beyond its acceptable tension level and become damaged. The connectors that connect the wire to the grounding jack may also become damaged.

For the above reasons, a more reliable grounding system and method are desired. In order to be more reliable, the grounding system has to provide a quick and easy way for operators to ground/de-ground themselves and reduce the chances that an operator will forget to ground/de-ground himself as is appropriate.

SUMMARY OF THE INVENTION

The invention pertains to a device, system, and method for grounding an operator such that it takes minimal effort on the part of the operator to get grounded. The invention provides the added benefit of automatically disengaging if the operator leaves a designated area, so that the operator does not have to remember to disconnect himself from the grounding device.

A magnetic connector for a wriststrap monitor terminal is also disclosed. The magnetic connector for the wriststrap is easily engageable and disengageable. The magnetic connector allows free movement of operator without disengaging of the wriststrap cord within desired range of movement of the operator, but easily disengages when the operator moves beyond the desired range. It is also desirable that disengagement of the connector does not result in the operator being hit by the wriststrap cord due to the spring action of coiled wriststrap cord. For some types of wriststrap monitors it is desirable to provide information on whether or not the wriststrap cord is connected to start monitoring proper operator's connection.

In accordance with the invention, a wriststrap connector is provided that includes a wriststrap cord connected to a wriststrap, one or more non-magnetic contacts that can be coupled to a terminal of a wriststrap monitor device, and a magnetic contact that can be magnetically coupled to the terminal of the wriststrap monitor device wherein the wriststrap connector is disengagably coupled to the terminal of the wriststrap monitor by the magnetic contact.

In accordance with another aspect of the invention, a wriststrap connector and monitor system is provided that has a wriststrap connector having a wriststrap cord connected to a wriststrap, one or more non-magnetic contacts that can be coupled to a terminal of a wriststrap monitor device and a magnetic contact that can be magnetically coupled to the terminal of the wriststrap monitor device wherein the wriststrap connector is disengagably coupled to the terminal of the wriststrap monitor by the magnetic contact. The system also has a terminal unit having a magnetic element that magnetically attracts the magnetic contact of the connector so that the connector is magnetically disengagably coupled to the terminal unit.

In accordance with yet another aspect of the invention, a magnetic connector system is provided that has a connector having a metallic portion and a unit having a receptacle into which the metallic portion is inserted when mating the connector to the unit, the receptacle further comprising a first magnetic element that attracts the metallic portion when the connector is mated with the receptacle, a bias member and a second magnetic element biased away from the metallic portion by the bias member wherein the second magnetic element establishes an electrical connection with the metallic portion as the second magnetic element is attracted to the metallic portion.

BRIEF DESCRIPTION OF THE DRAWINGS

FIGS. 1a-1d depict a magnetic embodiment of the grounding device in accordance with the invention;

FIG. 1e depicts an embodiment of the magnetic device in accordance with the invention;

FIGS. 2a-2d depict another magnetic embodiment of the grounding device in accordance with the invention;

FIG. 7 depicts a weighted retraction system in accordance with the invention;

FIGS. 9a and 9b are flowcharts depicting the basic operation of the base unit in the ground monitoring system;

FIGS. 9c and 9d depict alarm signal intensity as a function of time;

FIGS. 15a and 15b depicts a user interface device that may be used for the enhanced grounding system in accordance with the invention;

FIGS. 16a and 16b depict a method and system for grounding the operator with minimum movement restriction in accordance with the invention;

FIGS. 17A-17H illustrate an embodiment of the magnetic connector for a wriststrap monitor in accordance with the invention;

FIGS. 18A and 18B illustrate yet another embodiment of the magnetic connector for a wriststrap monitor in accordance with the invention;

FIGS. 20A-20C illustrate yet another embodiment of the magnetic connector for a wriststrap monitor in accordance with the invention;

FIG. 21 illustrates yet another embodiment of the magnetic connector for a wriststrap monitor in accordance with the invention;

FIGS. 22A-22D illustrate yet another embodiment of the magnetic connector for a wriststrap monitor in accordance with the invention;

FIGS. 23A and 23B illustrate an embodiment of the magnetic connector in accordance with the invention.

DETAILED DESCRIPTION OF A PREFERRED EMBODIMENT

Figure 3A:
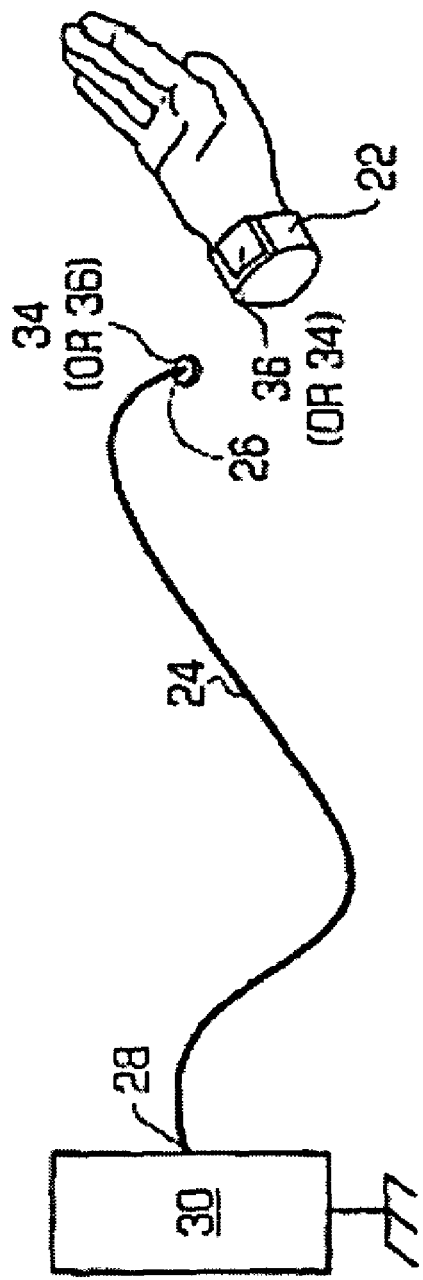
FIGS. 3a and 3b depict a Velcro-type embodiment of the grounding device in accordance with the invention.

The invention is particularly applicable to a user grounding system and it is in this context that the invention will be described. It will be appreciated, however, that the device and method in accordance with the invention has greater utility.

As used herein, a "designated area" is an area where an operator is required to be grounded, such as a workbench, the vicinity of a sensitive equipment, or a manufacturing area. Also, as used herein, the "first end" is the end of a coupling mechanism that is near the wristband worn by the operator and the "second end" is the end of the coupling mechanism that is near the grounded object. A "coupling mechanism" is a device, mechanism, or system for electrically coupling two points, including but not limited to a conventional cable, a metallic wire, a conductive wire, a conductive fabric, a synthetic wire/tape, or an insulative cord/tape that has a woven conductive strand. A "wristband" is any type of object that is shaped to be worn by a person and makes electrical contact with the person. A "fastening mechanism" is any device, mechanism, or system of electrically coupling the wristband to a grounded object in a releasable manner by coupling a mating structure with a fixing mechanism.

FIGS. 1a-1d, 2a-2d, 3a, 3b, and 4a-4d depict different embodiments of a grounding device 20 in accordance with the invention. The grounding device 20 includes a wristband 22 that is electrically coupled to a grounded object 30 with a self-disengaging fastening mechanism. The fastening mechanism includes a coupling mechanism 24 that securely connects the wristband 22 to the grounded object 30 and automatically disconnects the wristband 22' and/or the coupling mechanism from the grounded object 30 when the tension level of the coupling mechanism exceeds a threshold level, to prevent damage to the component that is being operated on. This secure connection is achieved by coupling a mating structure (e.g., a magnetic mating structure 40 or a mechanical mating structure 54 described below) with a fixing mechanism (e.g., a ferromagnetic fixing mechanism 30 or a mechanical fixing mechanism 52). The fixing mechanism is designed to release the mating structure in response to a certain level of force being applied to the mating structure. The mating structure and the fixing mechanism may use any conventional mechanism for releasably coupling two objects.

FIGS. 1a, 1b, 1c, and 1d depict a magnetic embodiment of the grounding device 20 in accordance with the invention. FIG. 1a depicts a first magnetic embodiment of the grounding device 20. In this embodiment, a first end 26 of the coupling mechanism 24 is connected to the wristband 22 and a second end 28 of the coupling mechanism 24 is connected to a magnetic mating structure 40 that is designed to be releasably coupled to the grounded object 30. The grounded object 30, in this embodiment, has a ferromagnetic fixing mechanism 32 to which the magnetic mating structure 40 can securely but releasably attach. The size of the magnetic mating structure 40 is controlled so that a moderate amount of tugging on the coupling mechanism 24 will cause it to detach from the ferromagnetic fixing mechanism 32, as indicated by an arrow 42. This way, if an operator forgets to disconnect the wristband 22 from the grounded object 30 before leaving the designated area, the magnetic mating structure 40 will self-disengage from the ferromagnetic fixing mechanism 32 when the coupling mechanism has a predetermined pulling force applied to it, such as when the operator is a certain distance away from the grounded object 30. A person of ordinary skill in the art would understand to set the length of the coupling mechanism 24 such that the magnetic mating structure 40 will not self-disengage when the operator is still in the designated area.

FIG. 1b depicts the magnetic embodiment of FIG. 1a when the magnetic mating structure 40 is attached to the ferromagnetic fixing mechanism 32 so that the user is grounded.

FIGS. 1c and 1d depict an alternative magnetic embodiment of the grounding device 20 in accordance with the invention. In this alternative embodiment, the positions of the ferromagnetic metal surface 32 and the magnetic mating structure 40 are changed relative to the embodiment in FIGS. 1a and 1b. Instead of the second end 28 of the coupling mechanism 24 being connected to the magnetic mating structure 40, it is connected to the ferromagnetic fixing mechanism 32. In this embodiment, the grounded object 30 includes the magnetic mating structure 40 that is positioned to be coupled with the ferromagnetic fixing mechanism 32, as shown in FIG. 1d. When an operator wearing the wristband 22 travels beyond the length of the coupling mechanism 24 or exerts a particular predetermined force on the coupling mechanism 24, the ferromagnetic fixing mechanism 32 automatically disengages from the magnet 48, as indicated by an arrow 46 (in FIG. 1c). A person of ordinary skill in the art would understand how to design such arrangements. This alternative embodiment of FIGS. 1c and 1d may be preferable to the embodiment of FIG. 1a and 1b if the presence of a magnet at the end of the coupling mechanism 24 is not desirable due to certain manufacturing conditions.

FIG. 1e depicts an embodiment of the magnetic mating structure 40 in accordance with the invention. In the embodiments of FIGS. 1a, 1b, 1c, and 1d, the magnetic mating structure 40 has to be both magnetic and electrically conductive. This can be achieved by using a material that is both magnetic and electrically conductive, or by mounting a magnetic material on an electrically conductive arrangement. If the magnetic mating structure 40 includes a magnetic material that is also electrically conductive, the magnetic material can be designed as part of the electrical connection. On the other hand, if the magnetic mating structure 40 includes a nonconductive magnetic material 42 (e.g., ceramics), the magnetic mating structure 40 may also include a metal casing or shell 44 to establish electrical connection between the coupling mechanism 24 and the ferromagnetic fixing mechanism 32.

The grounding of the operator does not require low resistance nor high current capacity. Therefore, it is possible to use more flexible and easily extendable material for the coupling mechanism 24 that would further improve convenience for operators and facilitate proper grounding.

FIGS. 2a-2d show yet another magnetic embodiment in accordance with the invention. Unlike in the embodiments of FIGS. 1a-1d, where the releasable attachment of the coupling mechanism 24 occurred near the second end 28 of the coupling mechanism 24, the releasable attachment occurs at the first end 26 in the embodiments of FIGS. 2a-2d. As in the embodiments of FIGS. 1a-1d, the magnetic mating structure 40 is both magnetic and electrically conductive. The embodiments of FIGS. 2a-2d may be preferred over the embodiments of FIGS. 1a-1d because the operator would not carry/drag around the coupling mechanism 24 upon leaving the designated area.

In the embodiment of FIGS. 2a and 2b, the first end 26 of the coupling mechanism 24 is connected to the magnetic mating structure 40 and the second end 28 is connected to the grounded object 30. In this embodiment, the wristband 22 has the ferromagnetic fixing mechanism 32 attached to it so that it can connect to the coupling mechanism 24 via the magnetic mating structure 40 as shown in FIG. 2b.

The embodiment of FIGS. 2c and 2d is similar to the embodiment of FIGS. 2a and 2b except that the positions of the ferromagnetic fixing mechanism 32 and the magnetic mating structure 40 are changed. In the embodiment of FIGS. 2c and 2d, the first end 26 of the coupling mechanism 24 is connected to the ferromagnetic fixing mechanism 32 and the second end 28 is connected to the grounded object 30. The wristband 22 includes the magnetic mating structure 40 that couples to the ferromagnetic fixing mechanism 32, as shown in FIG. 2d.

Figure 3B:
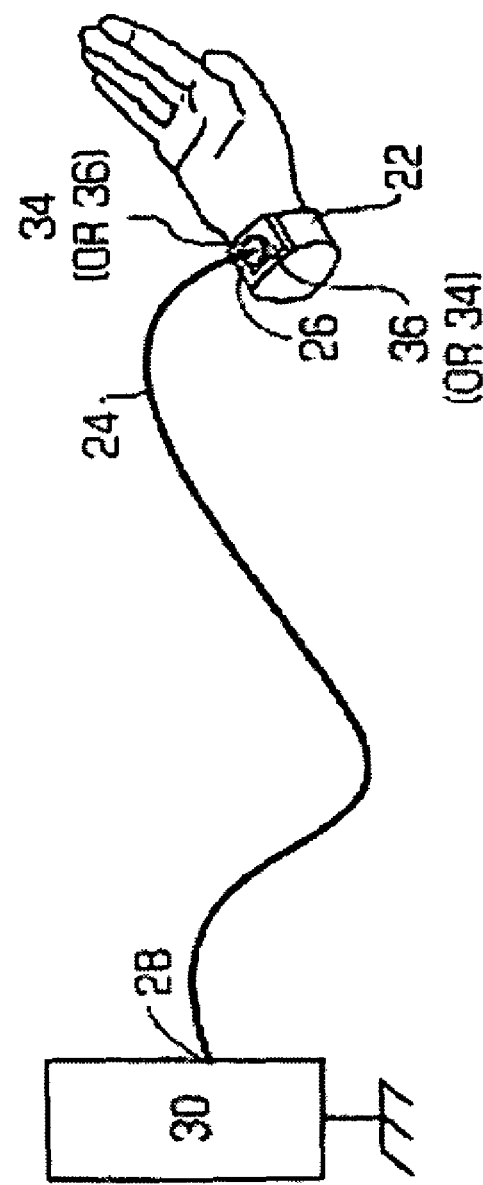

FIGS. 3a and 3b depict a Velcro-type embodiment of the grounding device 20 in accordance with the invention. This Velcro-type embodiment is similar to the magnetic embodiment described above except that a Velcro is used as the fastening mechanism instead of the magnetic mating structure 40 and the ferromagnetic fixing mechanism 32. The Velcro-based fastening mechanism includes a loop-type mating structure 34 and a hook-type fixing mechanism 36, as shown in FIGS. 3a and 3b. The Velcro that is used herein has a conductive portion to allow proper grounding of the wristband 22. The Duo-lock type fastening mechanism (manufactured by 3M Corporation) may be used. As indicated in parenthesis, the positions of the loop-type mating structure 34 and the hook-type fixing mechanism 36 may be switched.

Figure 4B:
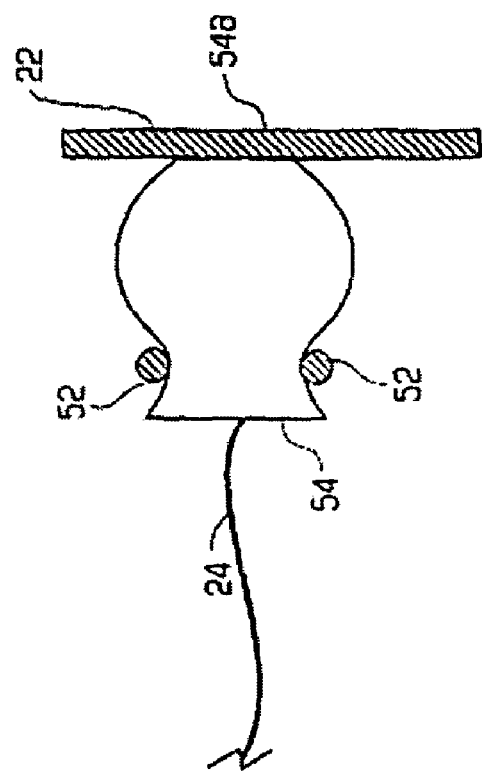
FIGS. 4a-4d depict a mechanical embodiment of the grounding device in accordance with the invention.
Figure 4D:
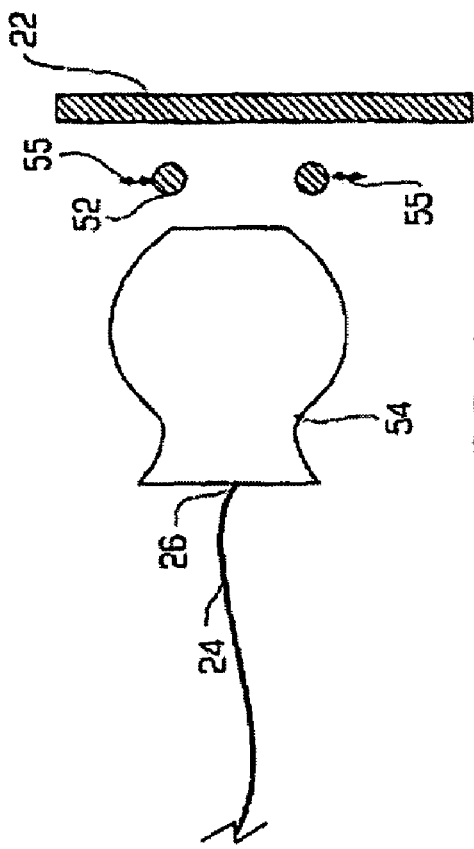
Figure 4A:
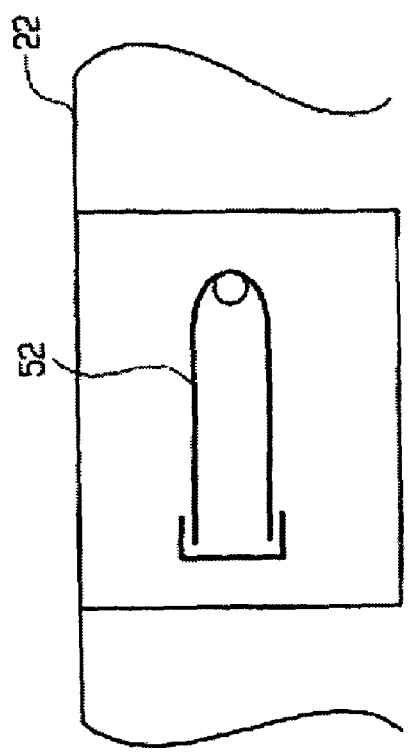
Figure 4C:
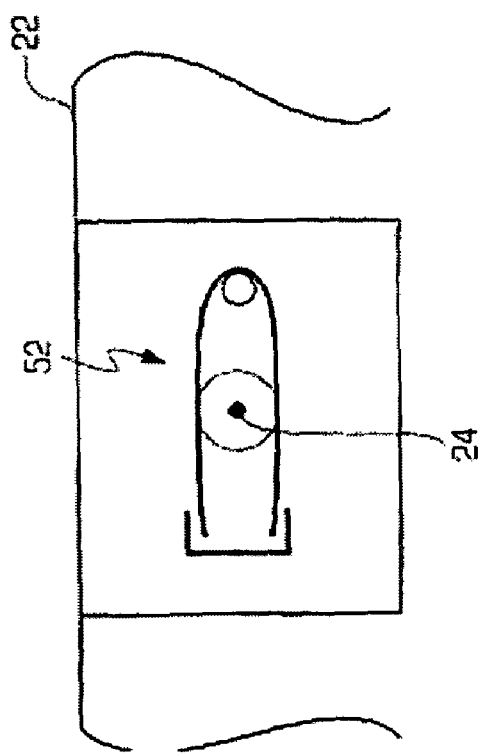

FIGS. 4a, 4b, 4c, and 4d depict a mechanical embodiment of the grounding device 20 in accordance with the invention. FIGS. 4a and 4c are top views and FIGS. 4b and 4d are side views. The mechanical embodiment achieves the same function as the magnetic embodiment, but without using magnetic material. Instead of using the magnetic mating structure 40 and the ferromagnetic fixing mechanism 32, the mechanical embodiment utilizes a mechanical mating structure 54 and a mechanical fixing mechanism 52. FIG. 4a shows an exemplary fixing mechanism 52 attached to a wristband 22. The mechanical fixing mechanism 52 is any type of mechanism that would hold the mechanical mating structure 54 in place and release it in response to a pulling force. For example, the mechanical fixing mechanism 52 may include a spring-loaded contact so that the mechanical mating structure 54 can be inserted or withdrawn as the spring-loaded contact moves in the directions shown by arrows 55. The mechanical mating structure 54 is connected to the first end 26 of the coupling mechanism 24. The mechanical mating structure 54 either has an electrically conductive section 54a or accommodates the coupling mechanism 24 so that the coupling mechanism 24 mates with the electrically conductive portions of the wristband 22 when the mechanical mating structure 54 is held by the mechanical fixing mechanism 52. The mechanical mating structure 54 is shaped to easily and securely become engaged with the wristband 22 (see FIGS. 4c and 4d) while becoming disengaged from the spring-loaded contact by a moderate amount of pulling.

The embodiments described in FIGS. 1a-1d, 2a-2d, and 4a-4d provide a way of easily and securely coupling the wristband 22 to the grounded object 30 in a way that also allows decoupling when a sufficient force is applied to the coupling mechanism 24, for example if the wristband 22 and the grounded object 30 are separated by a distance longer than the length of the coupling mechanism 24. A minimal effort is needed on the part of the operator to become grounded (i.e., couple the wristband 22 to the grounded object 30), and no effort is needed to disengage the ground connection when the operator leaves the designated area since the wristband 22 and the grounded object 30 are releasably coupled.

After the fastening mechanism disengages to decouple the wristband 22 from the grounded object 30, the coupling mechanism 24 could be left lying on the floor or be dragged around by the operator, interfering with foot traffic and possibly causing a dangerous situation. FIG. 5a depicts a spring-loaded spool 70 that may be used to automatically retract the coupling mechanism 24 after the grounding device 20 is disengaged from the grounded object 30. The spring-loaded spool 70 may be designed to maintain a comfortable level of tension in the coupling mechanism 24 when the wearer of the wristband 22 walks around, so that when the tension level drops due to either the disengagement of the wristband 22 from the grounded object 30 or the discontinued use of the wristband 22 by the operator, the spool is triggered automatically to retract the coupling mechanism 24. Optionally, a well-known ratchet mechanism (not shown) may be incorporated into the spool 70 to hold the coupling mechanism 24 in the extended state so that the operator is not constantly pulled by the spring-loaded spool 70. This spring-loaded spool 70 may be used for any embodiment of the grounding device 20 described above.

Figure 5B:
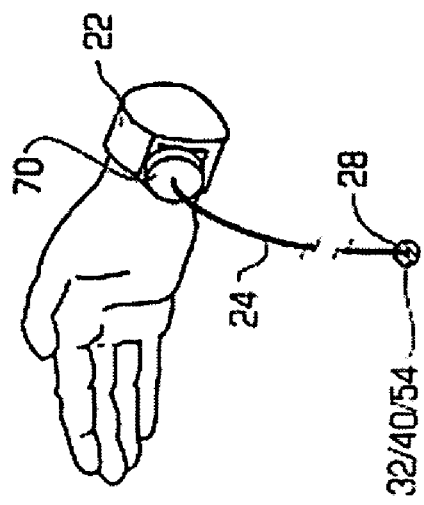
FIGS. 5a and 5b depicts a spring-loaded spool that may be used to automatically retract the coupling mechanism after the grounding device is disengaged from the grounded object.
Figure 5A:
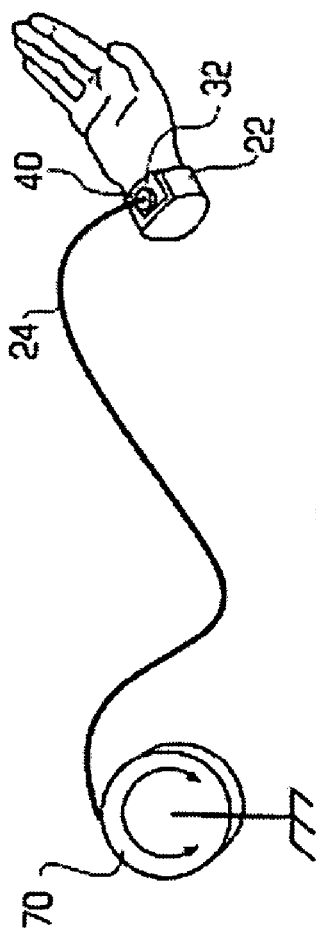

FIG. 5b depicts an embodiment of the grounding device 20 wherein the spool 70 is attached to the first end 26 of the coupling mechanism 24 instead of the second end 28. As shown, the spring-loaded spool 70 may be attached to the wristband 22. A mating structure such as a magnetic mating structure 40 or a mechanical mating structure 54 may be attached to the second end 28 of the coupling mechanism 24. Alternatively, a fixing mechanism such as a ferromagnetic fixing mechanism 32 may be attached to the second end 28.

Figure 6B:
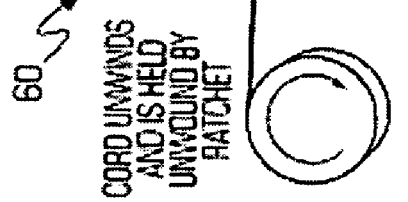
FIGS. 6a and 6c depict a grounding system including the spring-loaded spool of FIG. 5a and the grounding device of FIGS. 2a and 2b.
Figure 6A:
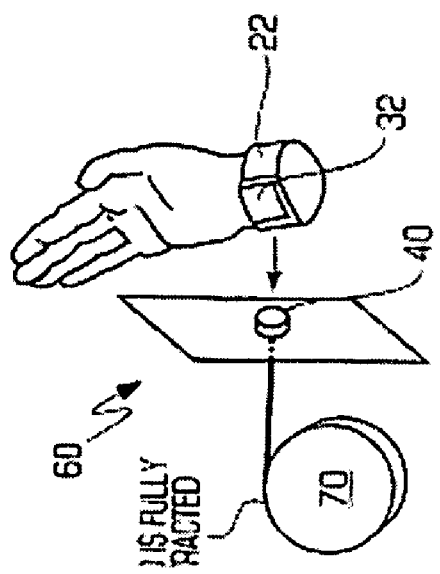

FIGS. 6a-6c depict a grounding system 60 including the spring-loaded spool 70 of FIG. 5a and the grounding device 20 of FIGS. 2a and 2b. An operator grounds himself by putting on the wristband 22 and touching the magnetic mating structure 40 with the ferromagnetic fixing mechanism 32 on his wristband 22. When the operator moves away from the spring-loaded spool 70, the coupling mechanism 24 is automatically extended to allow unrestricted movement for the operator, as shown in FIG. 6b. After the operator disengages from the cable 24, the coupling mechanism 24 is retracted in by the spring-loaded spool 70, as shown in FIG. 6c. The invention is not limited to a specific way in which the retraction of the coupling mechanism 24 is triggered. For example, if the spring-loaded spool 70 is designed to maintain a constant level of tension in the coupling mechanism 24 as mentioned above, the retraction will automatically happen when the fastening mechanism is disengaged. Alternatively, the retraction may be triggered by the operator's sharply tugging the coupling mechanism 24 to release a latch. If a ratchet mechanism is used, a detector circuit may be used to release the ratchet latch that was holding the coupling mechanism 24 in its extended position. A circuit may be used to detect that the fastening mechanism is disengaged and activate an electric motor to retract the cable 24.

FIG. 7 depicts a weighted retraction system 80 that may be used instead of or in combination with the spring-loaded spool 70 to handle the coupling mechanism 24 when the grounding device 20 is not in use. The weighted retraction system 80 includes a weight 84 connected to one end of the coupling mechanism 24 and a pulley 86 that controls the position of the weight 84. The pulley effectively translates the vertical motion of the weight 84 into a horizontal force that pulls in the coupling mechanism 24. Once the fastening mechanism is disengaged, the retraction may continue until a stopper 82 (which may be, for example, the magnetic mating structure 40) comes in contact with a plate 83 through which the coupling mechanism 24 extends. The plate 83 may be grounded. The weighted retraction system 80 may be used with the embodiments of FIGS. 2a-2d where the detachment occurs at the first end 26 of the coupling mechanism 24. A person of ordinary skill in the art would understand to adjust the weight 84 so that it is not too heavy for the wearer while the grounding device 20 is in use.

The abovementioned methods and devices for retracting the coupling mechanism 24 may also be accomplished using gravity-driven retraction mechanisms or electric drive (i.e., motor) based mechanisms.

Figure 8:
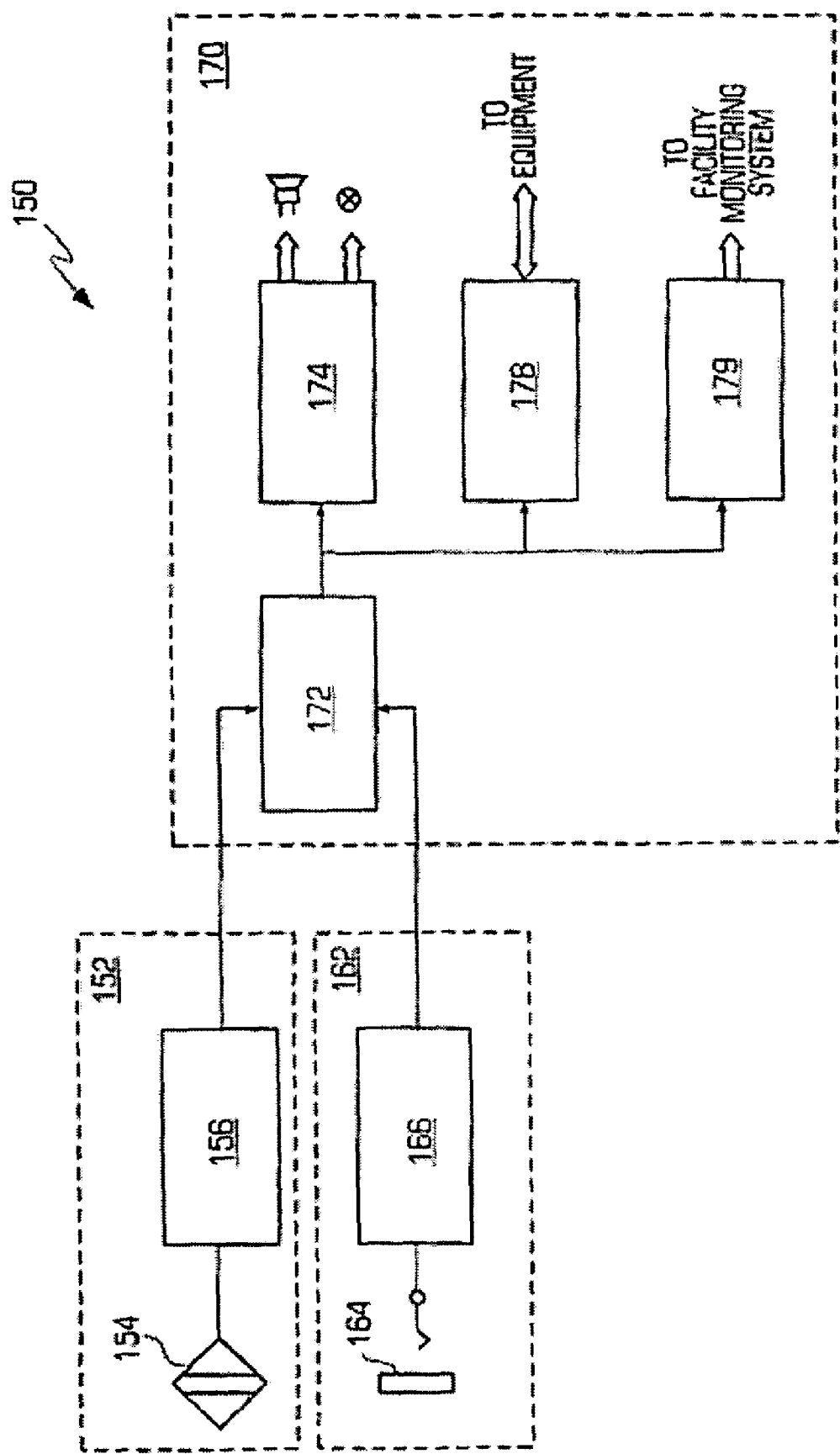
FIG. 8 depicts a generalized block diagram of an enhanced grounding system in accordance with the invention.

While the grounding system 60 provides numerous advantages over the currently used system, it does not prevent an operator from forgetting to ground himself or alert the operator if the fastening mechanism accidentally becomes disengaged. The grounding system 60 above cannot distinguish between a potentially dangerous situation where the operator forgets to use the grounding device 20 from a safe situation where the operator has gone home. In order to distinguish the potentially dangerous situation from the safe situation, it is desirable to determine not only whether the grounding device 20 is in use but also whether the operator is in the designated area. FIG. 8 depicts an enhanced grounding system 150 that monitors whether the grounding device 20 is in use and even determines whether the grounding device 20 should be in use. An alarm signal may be triggered if the operator is on the premises without being properly grounded. In addition, a signal can be issued to equipment to halt its operation should an ungrounded operator attempt access to sensitive components or a sensitive area.

FIG. 8 depicts a generalized block diagram of the enhanced grounding system 150 in accordance with the invention. The grounding system 150 includes a proximity sensing unit 152, a grounding device monitoring unit 162, and a base unit 170. The proximity sensing unit 152, which senses whether the operator is in a designated area, includes a proximity sensor 154 and, if desired/needed, a circuit 156. The proximity sensor 154 may be implemented by any device(s) deemed suitable by a person of ordinary skill in the art, such as an infrared motion detector, an ultrasonic proximity sensor, a microwave proximity sensor, a light barrier, or a mechanical detection means using a pressure mat. The circuit 156 transforms the output of the proximity sensor 154 to provide enabling signals to a logic circuit 172 in the base unit 170. In one embodiment, the grounding device monitoring unit 162 and/or the base unit 170 remain in a stand-by mode or a disabled mode until the proximity sensing unit 152' senses that the operator is in the designated area. In response to sensing operator presence, the grounding device monitoring unit 162 and/or the base unit 170 become enabled. In another embodiment, just the alarm may remain in a stand-by mode and become enabled upon detecting operator presence.

The grounding device monitoring unit 162, which monitors whether the grounding device 20 is in use, includes a detector 164. The detector 164 may detect whether the wristband 22 is grounded, for example by implementing the arrangement shown below in FIGS. 13a and 13b. Like the proximity sensor 154, the probe 164 feeds information to the base unit 170. A wristband monitoring circuit 166 may be incorporated into the grounding device monitoring unit 162 to properly process the probe reading for the base unit 170. The grounding device monitoring unit 162 may also incorporate information about whether the wristband 22 is worn properly, for example by reading the difference between the two wires in the device of FIGS. 14a-14c. The wrist strap monitoring circuit 166 may be of any construction deemed suitable by a person of ordinary skill in the art, as long as it provides pass/fail signals indicating whether the operator is wearing the wristband properly.

A logic circuit 172 in the base unit 170 processes the signal from the proximity sensing unit 152 and the signal from the grounding device monitoring unit 162 to determine if an alarm needs to be issued. An alarm circuit 174 is triggered only if the signal from the proximity sensing unit 152 indicates that the operator is in the designated area and the grounding device monitoring unit 162 indicates that the grounding device 20 is not in use. The grounding device 20 is not in use if either the wristband 22 is not grounded or the wristband 22 is grounded but the operator is not wearing the wristband properly. The alarm could be in the form of light 175 and/or sound 176 signals. Optionally, a connection or signal may be provided to an equipment interface 178, which is connected to the equipment that requires the operator to be grounded. The equipment, upon receiving the signal from the equipment interface 178, may either halt the equipment operation and/or issue an additional alarm. A signal may also be forwarded to a facility monitoring system 179, which maintains a log of when the alarm was issued. Although this particular embodiment employs logic circuits, the invention is not limited to logic circuit embodiments and the same function can be performed by other arrangements (e.g., a microcontroller) without departing from the spirit of the invention.

FIG. 9a is a flowchart depicting the basic operation of the base unit 170 in the ground monitoring system 150. As the flowchart shows, the base unit 170 receives input from the proximity sensing unit 152 regarding whether the operator is in the designated area (stage 190). If the operator is in the designated area (stage 192), the base unit 170 checks if the operator is grounded (stage 194). If the operator is not grounded, then an alarm is triggered (stage 196). The alarm is not triggered if either the operator is not in the designated area or the operator is in the designated area and properly grounded. The operator is properly grounded when the wristband 22 is grounded and making proper contact with the operator. When no alarm is issued, the base unit 170 waits a predetermined period of time and restarts the process at stage 190.

FIG. 9b is a flowchart depicting the detailed operation of the base unit 170. Unlike the process of FIG. 9a, this process takes into account the time it takes an operator to get grounded once he enters the designated area. In this process, after sensing the presence of the operator in the designated area, the base unit 170 waits a certain amount of time before checking if the operator is grounded. If the operator is not grounded at the end of the grace period, the alarm is triggered.

Referring to the flowchart in FIG. 9b, the base unit 170 receives input from the proximity sensing unit 152 regarding whether the operator is in the designated area (stage 200). If the operator is in the designated area (stage 202), the base unit 170 waits a predetermined grace period for the operator to get grounded (stage 204). At the end of the grace period, the base unit 170 checks if the operator is grounded (stage 206) and triggers the alarm (stage 208) if the operator is not grounded. After the alarm, the base unit 170 waits for another predetermined period of time (stage 210) before checking again to see if the operator has been grounded. If the operator is still not grounded, the alarm is triggered again (stage 214). Optionally, at this point, a signal may be issued to the equipment (stage 216), for example to enable/disable the equipment so that the operator cannot operate the equipment without first grounding himself. A signal may also be sent to the facility monitoring system (stage 218) so that the fact that the alarm was triggered can be logged. Information regarding the proximity and status of the operator may be provided to the facility monitoring equipment. If the operator grounded himself after the first alarm (stage 212), then the base unit 170 monitors the connection (stage 219). Once it is detected that the grounding device 20 is no longer in use (stage 220), the process starts over.

In one embodiment, the first alarm that is issued in stage 208 may be in a form of temporally spaced bursts of sound and/or light. The frequency of the alarm bursts may gradually increase until it reaches the frequency level that is associated with the second alarm of stage 214. FIG. 9c, which shows the alarm signal intensity as a function of time, visually depicts the change in frequency. While FIG. 9c depicts the case where the operator does not ground himself after the first alarm, FIG. 9d depicts the case where the operator grounds himself after the first alarm, preventing the beeping/flashing frequency from increasing to the level of the second alarm. The alarm stops when the operator properly grounds himself. If the wristband 22 accidentally becomes disengaged from the grounding jack, the base unit 170 would detect the disengagement in stage 220 and issue the alarm in stage 208. In some embodiments, the alarm cycle repeats (first alarm, then second alarm) until either operator grounds himself or leaves the area.

Figure 10:
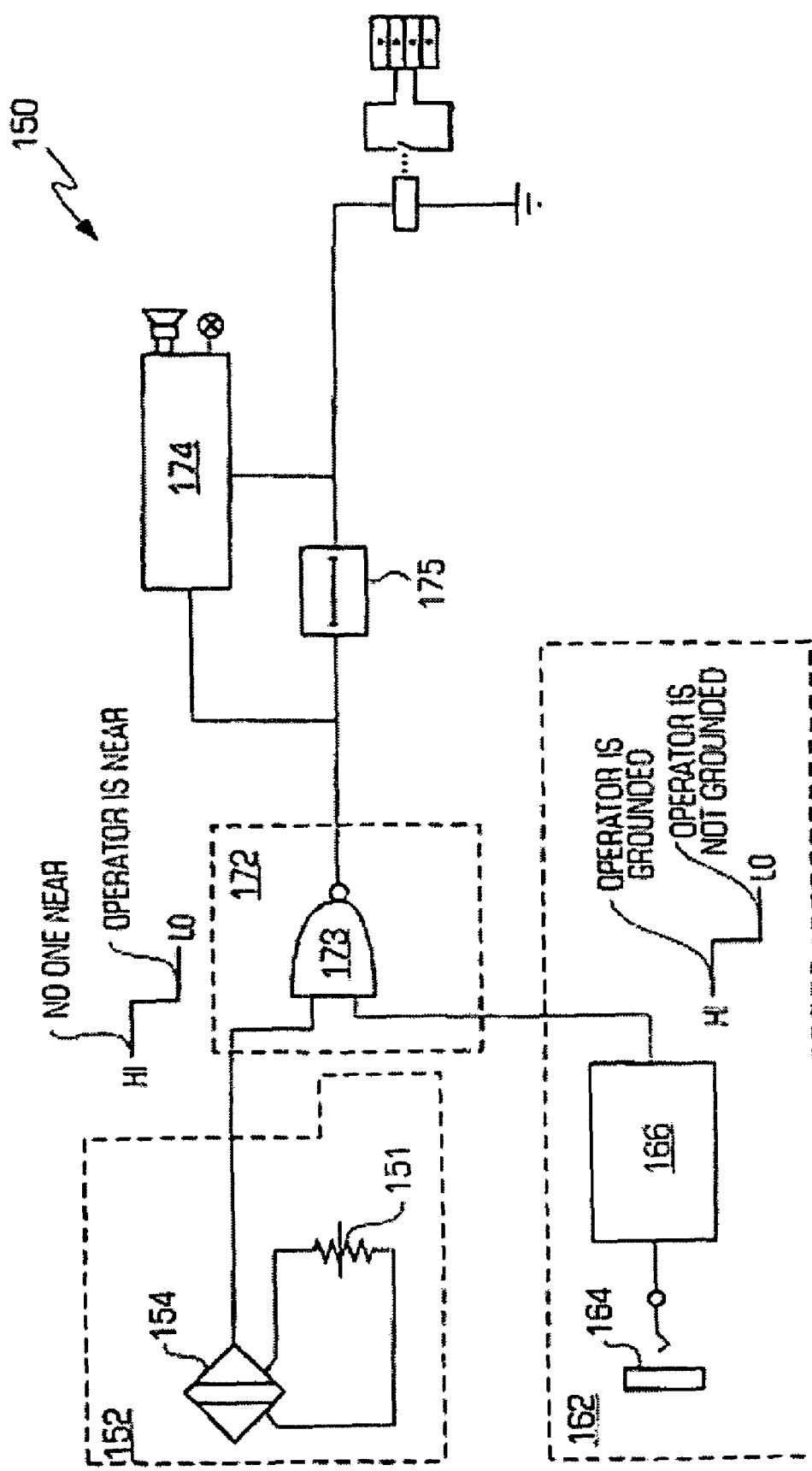
FIG. 10 depicts the enhanced grounding system in accordance with one embodiment of the invention.

FIG. 10 depicts the enhanced grounding system 150 in accordance with one embodiment of the invention. In the particular embodiment that is shown, the proximity sensing unit 152 is implemented with an infrared pyrosensor (motion detector) combined with optional sensitivity adjustment device 151 (e.g., a means for continuous adjustment such as a tuner or a potentiometer, or alternatively, a switch), which a person of ordinary skill in the art would know how to implement. The motion detector may be an infrared motion detector, an infrared proximity sensor, a microwave proximity detector, an ultrasonic proximity detector, a light barrier, or a mechanical detecting mechanism. If a motion is detected, the proximity sensing unit 152 outputs a low signal; if no motion is detected, it outputs a high signal. The grounding device monitoring unit 162 outputs a low signal if the operator is not grounded and a hi signal if the operator is grounded. The logic circuit 172 of the base unit 170 includes an a NAND gate 173 that is designed to trigger an alarm only if both the signal from the proximity sensing unit 152 and the signal from the grounding device monitoring unit 162 are low. The base unit 170 also includes a time delay unit 175 that gives the operator a grace period to get grounded.

Figure 11:
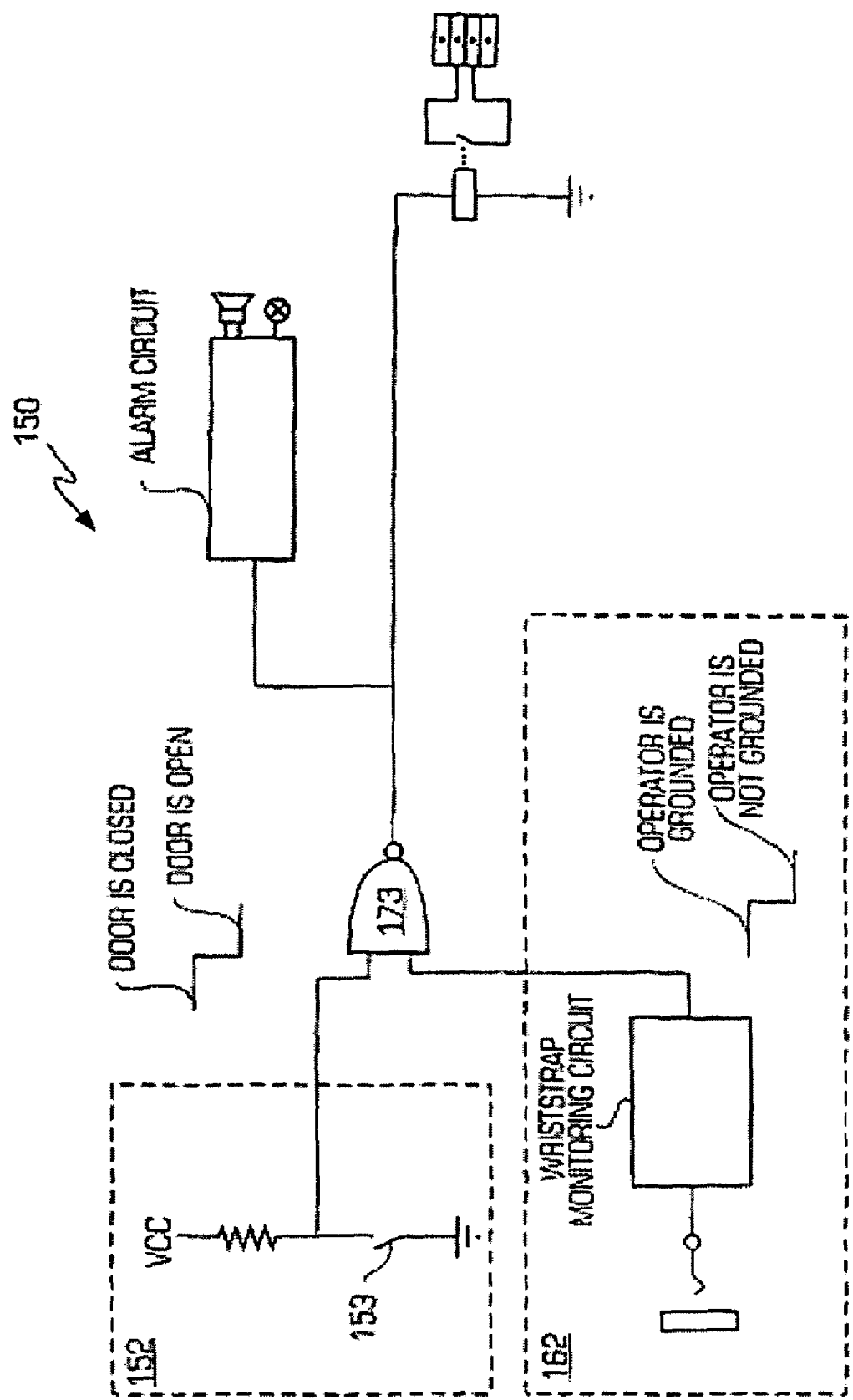
FIG. 11 depicts the enhanced grounding system in accordance with another embodiment of the invention.

FIG. 11 depicts the ground monitoring system 150 in accordance with another embodiment of the invention. This embodiment is similar to the embodiment of FIG. 10, with the main difference being that the proximity sensing unit 152 includes a safety access switch 153 for various equipments (such as access hatch, door, etc.) instead of the motion detector 154. The switch 153 does not permit use of the equipment until the switch is closed. In this embodiment, a time delay unit may not be necessary since an operator must be grounded prior to gaining access to the equipment.

Figure 12:
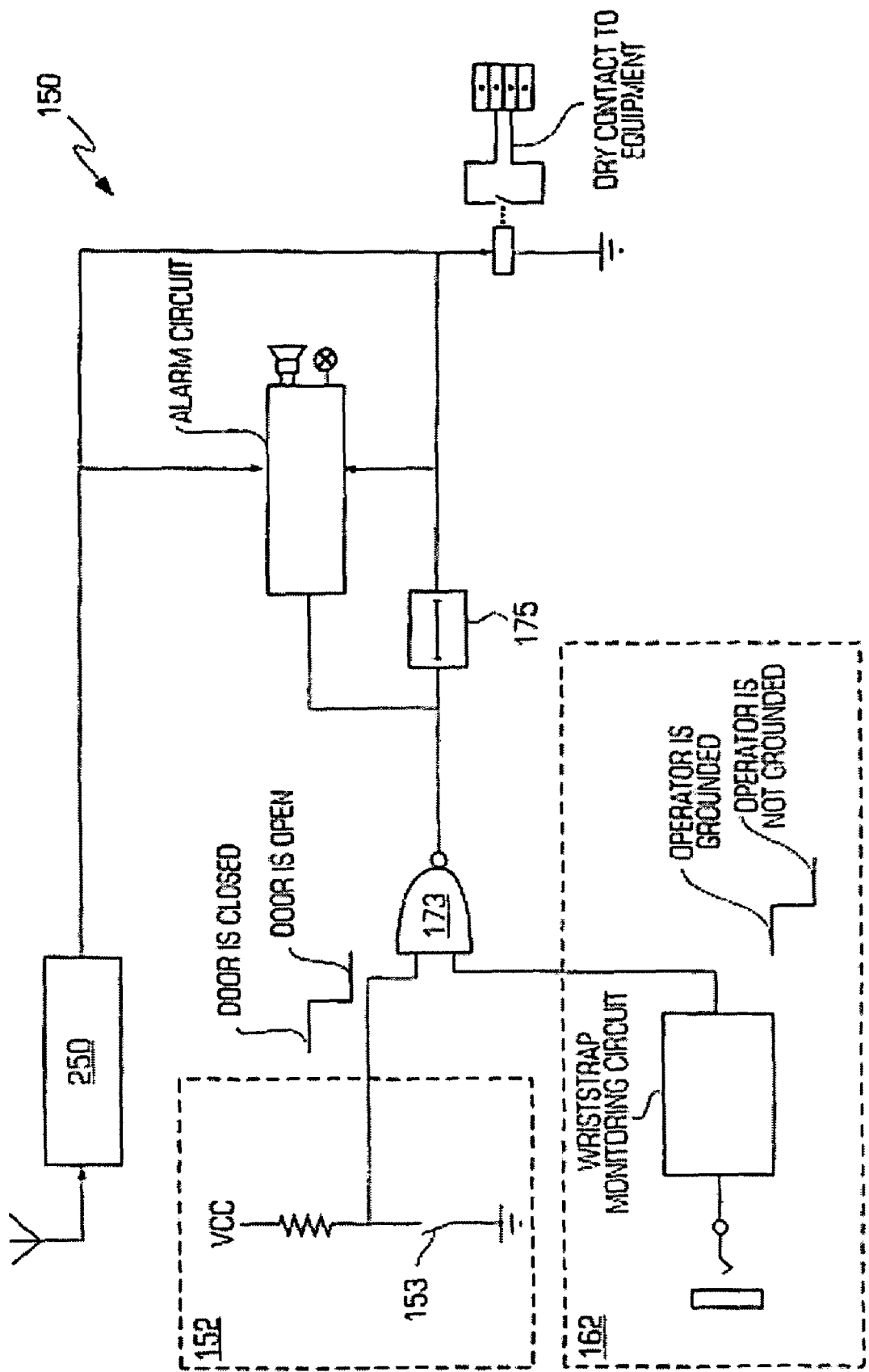
FIG. 12 depicts the enhanced grounding system in accordance with yet another embodiment of the invention.

FIG. 12 depicts the enhanced grounding system 150 in accordance with yet another embodiment of the invention. This embodiment is similar to the embodiment of FIG. 11 combined with an electrostatic voltage sensor 250 that restricts access to equipment if electrostatic voltage is present, providing an extra layer of protection. With this embodiment, if an operator brings a charged object to the equipment, the alarm will be triggered and/or access to the equipment will be denied until the charge is dissipated even if the operator is properly grounded. Electrostatic voltage sensor may be of any available construction, such as EM Aware ESD monitor by Credence Technologies (ftp://credencetech.com/pub/credence/EMAware.pdf).

Figure 13A:
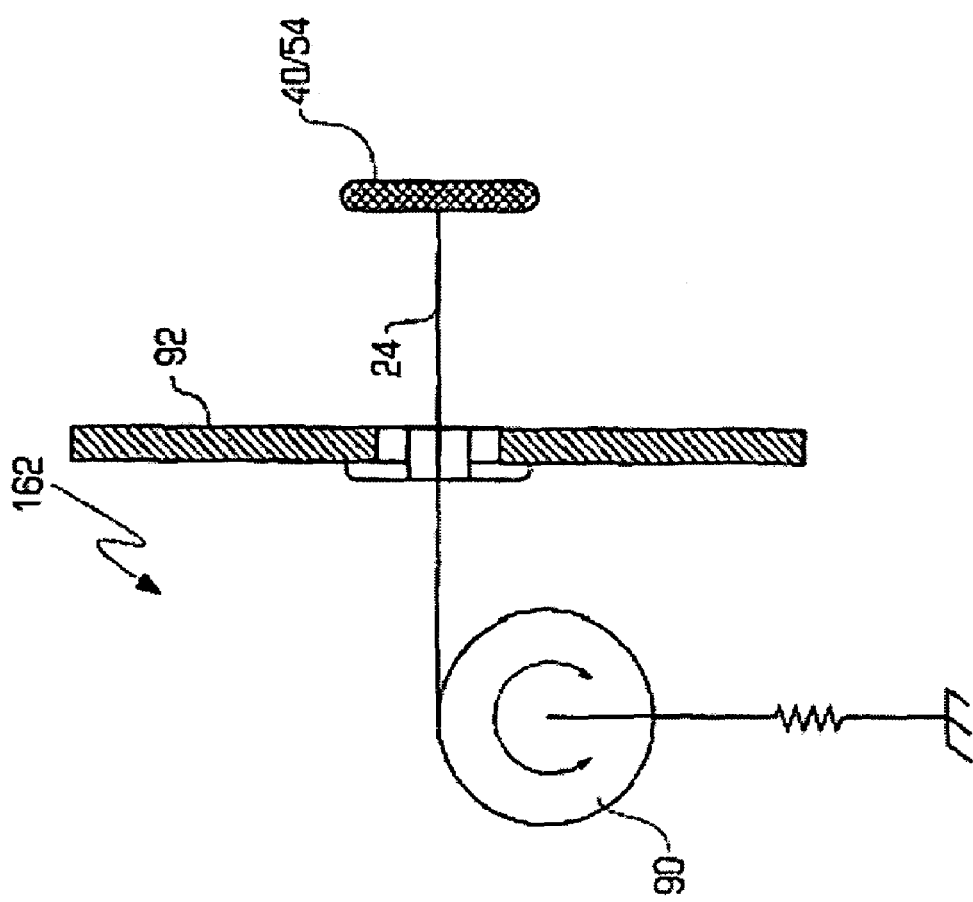
FIGS. 13a and 13b depict one embodiment of the grounding device monitoring unit in accordance with the invention.
Figure 13B:
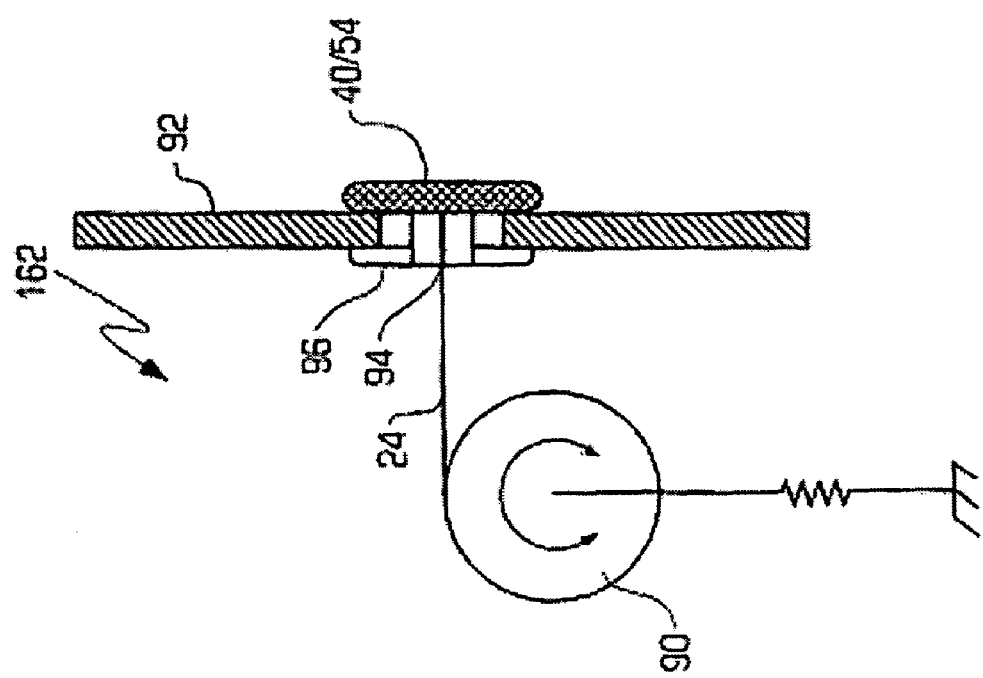

FIGS. 13a and 13b depict one embodiment of the grounding device monitoring unit 162 in accordance with the invention. This grounding device monitoring unit 162 monitors the voltage difference between a conductive plate 92 and a grounded rotating device 90. The grounded rotating device 90 may be the spring-loaded spool 70 (see FIG. 5a), the pulley 86 (see FIG. 7), or another device. The conductive plate 92, which may be the cover of a piece of equipment, has a hole 94 through which the coupling mechanism 24 extends to contact the grounded rotating device 90. There is an insulating region 96 that separates the hole 94 from the conductive plate 92. The grounded rotating device 90 is electrically coupled to the magnetic mating structure 40 (which may alternatively be a mechanical mating structure 54) through the coupling mechanism 24. When the grounding device 20 is in use, as shown in FIG. 13b, the conductive plate 92 is not electrically coupled to the grounded rotating device 90. However, when the grounding device is not in use, the grounded rotating device 90 retracts the coupling mechanism 24 to the point where the magnetic mating structure 40 contacts the conductive plate 92. When the magnetic mating structure 40 contacts the conductive plate 92, the conductive plate 92 also becomes grounded. Thus, by monitoring whether the conductive plate 92 is grounded or not, the grounding device monitoring unit 162 can tell if the grounding device 20 is in use.

Figure 14C:
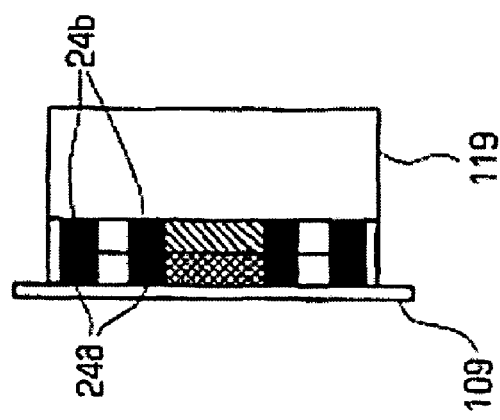
FIGS. 14a-14c shows an embodiment of a magnetic mating structure in accordance with the invention.
Figure 14B:
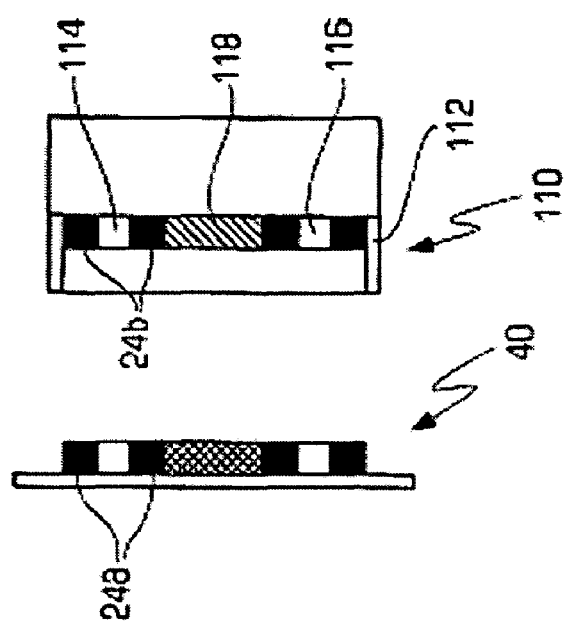
Figure 14A:
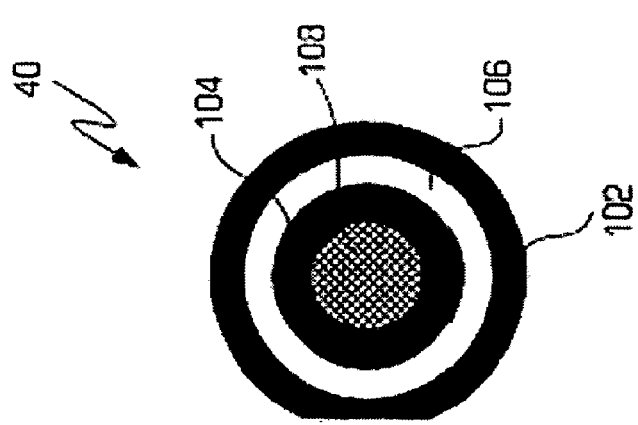

FIG. 14a shows an end view/cross section of embodiment of a magnetic mating structure 40 in accordance with the invention. The magnetic mating structure 40 includes an outer conductive ring 102 and an inner conductive ring 104 separated by an insulating region 106. Inside the inner conductive ring 104 is a magnetic material 108, although the specific location of the magnetic material 108 is not a limitation of the proposed invention. As shown in FIG. 14b, the magnetic mating structure 40 is mated with a ferromagnetic device 110, which also has an outer conductive ring 112 and an inner conductive ring 114 with an insulating region 116 between the two rings. Inside the inner conductive ring 114 is a ferromagnetic material 118. Preferably, the ferromagnetic device 110 has similar dimensions as the magnetic mating structure 40 so that the two parts can be mated easily as shown in FIG. 14c.

Since the outer conductive ring 102 is electrically insulated from the inner conductive ring 104 and the outer conductive ring 112 is electrically insulated from the inner conductive ring 114, it is possible to use up to two sets of two coupling mechanisms 24 with this embodiment. When the magnetic mating structure 40 is mated with the ferromagnetic device 110, each of the coupling mechanisms 24a mates with one of the coupling mechanisms 24b, creating two terminals. By monitoring the electrical continuity between the inner-ring terminal that connects a first set of coupling mechanisms 24a and 24b and the outer-ring terminal that connects a second set of coupling mechanisms 24a and 24b, it can be determined whether the operator is properly grounded. Electrical continuity between the two terminals indicates that the wristband is electrically coupled to the wearer. Thus, the embodiment of FIGS. 14a-14c help detect a situation where the user is wearing the wristband incorrectly so that the wristband is not making proper electrical contact with the user. This embodiment of the magnetic mating structure 40 may be used in the grounding device monitoring unit 162 of FIG. 13a and FIG. 13b. The configuration of the magnetic mating structure 40 and the ferromagnetic device 110 shown here provide the additional benefit of being difficult to break/damage.

A shell 109 that supports the magnetic mating structure 40 contacts a shell 119 that supports the ferromagnetic device. The shells 109 and 119 may be electrically conductive, depending on the embodiment. A person of ordinary skill in the art would understand that other devices may be used to detect whether the wristband 22 is worn properly, such as the single-wire device Jewel™ made by Desco, and any of these devices may be used to implement the grounding device monitoring unit 162.

FIG. 15a depicts a user interface device 180 that may be used for the enhanced grounding system 150 in accordance with the invention. The user interface device 180 includes a connector 181 through which the wristband 22 is coupled to the grounded object 30. This connector 181 could be of one of the magnetic/mechanical configurations described above or any other conventional configurations. The user interface device 180 further includes the proximity detector 154 and a switch/tuner 182 for adjusting the sensitivity of the proximity detector 154. There is also a pass LED 175a and a fail LED 175b and a speaker or a buzzer 176 that are used to alert the operator (see, e.g., stages 208 and 214 in FIG. 9b) that he needs to ground himself.

FIG. 15b depicts a connecting mechanism 186, which may be a terminal block or a connector, that provides power to the user interface device 180 and also provides output to various equipment. A power LED light 185 (see FIG. 15a) indicates whether the user interface device 180 is connected to the connecting mechanism 186.

For operators, it is often important to be free of constraints while wearing the grounding device 20. Conventional grounding devices tend to limit operator movements because of the coupling mechanism that freely hangs from the wristband. The hanging coupling mechanism that interferes with movement provides one more reason for operators to not properly ground themselves.

FIGS. 16a and 16b depict a method and device for grounding the operator with minimum movement restriction in accordance with the invention. As shown in FIG. 16a, the operator wears a wristband 22 that is connected to the coupling mechanism 24. The coupling mechanism 24 is channeled either over or under the operator's garment and couples to a connector 260. The connector 260 connects a first section 24c of the coupling mechanism that extends from the wristband 22 to a second section 24d of the coupling mechanism that extends from the grounded object 30, and may be worn in a way that does not limit the operator's movements. For example, as shown in FIG. 16a, the connector 260 may be attached to a belt 262. The connector 260 may be designed so that either the first section 24c or the second section 24d, or both, may be unplugged from it. As shown in FIG. 16b, one or more garters 264 may be worn around the arm to keep the first section 24c of the coupling mechanism close to the body so that the hanging coupling mechanism is unlikely to interfere with the operator's activity. As described above, the coupling mechanism 24 can be automatically retracted (e.g., by a spool) once the operator disengages the fastening device. A spool may be incorporated into the connector 260.

FIG. 16b depicts an operator working while wearing the grounding device 20 of FIG. 16a. As shown, the grounding device 20 does not impede the operator's movements.

Now, several embodiments of a magnetic connector for a wriststrap monitor terminal will be described. Similar to the embodiments already described, the magnetic connector for the wriststrap has to be easily engageable and disengageable. The connector should allow free movement of operator without disengaging of the wriststrap cord within desired range of movement of the operator, but easily disengage when the operator moves beyond the desired range. It is also desirable that disengagement of the connector does not result in the operator being hit by the wriststrap cord due to the spring action of coiled wriststrap cord. For some types of wriststrap monitors it is desirable to provide information on whether or not the wriststrap cord is connected to start monitoring proper operator's connection. Several specific examples of connectors for wriststrap monitors are described below, but it should be understood that other connectors that can be made are within the scope of this invention since the invention should not be limited to the particular examples disclosed herein.

Figure 17H:
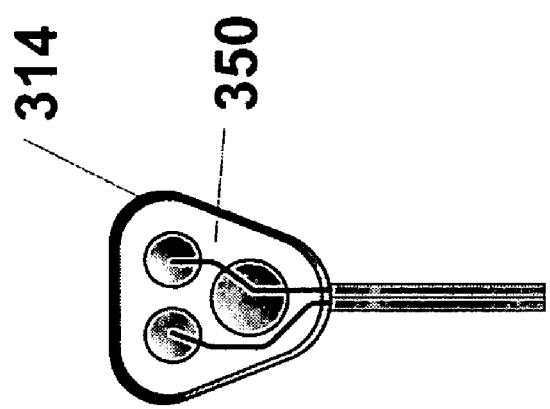
Figure 17G:
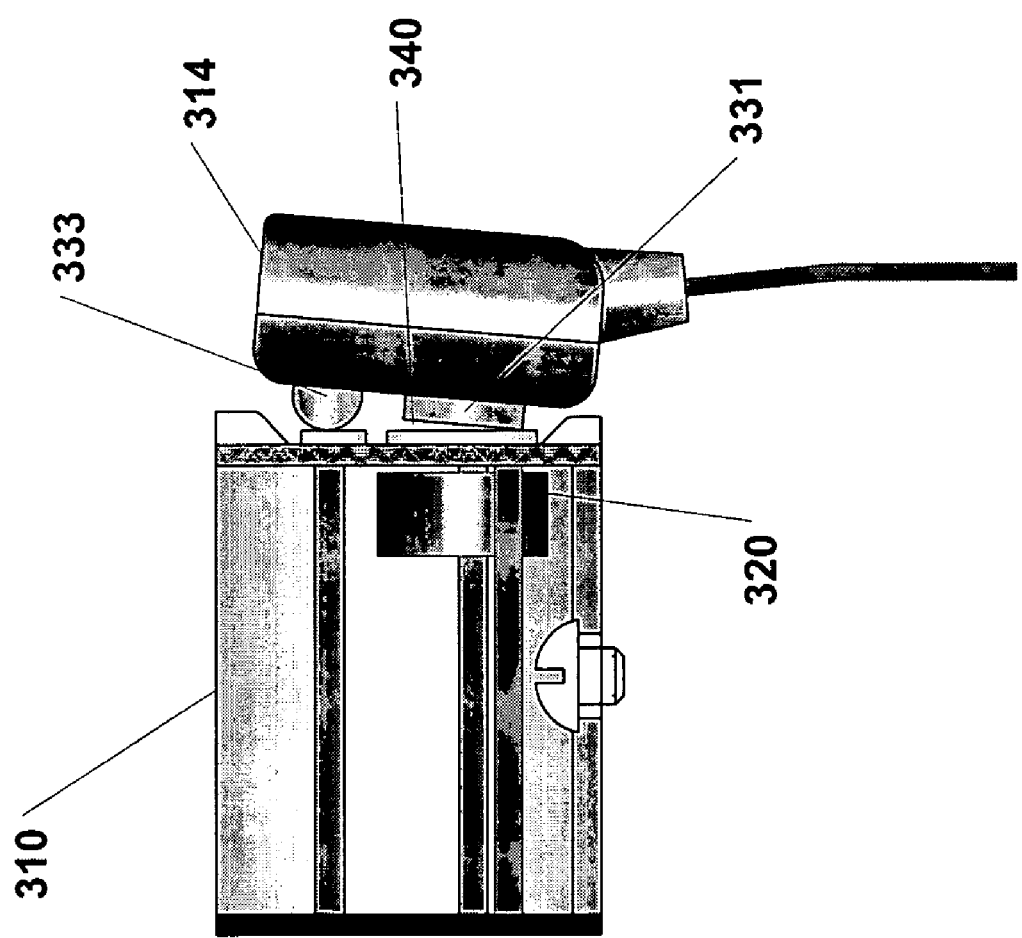

FIGS. 17A-17H illustrate an embodiment of the magnetic connector for a wriststrap monitor 310 in accordance with the invention. The wriststrap monitor terminal 310 (FIG. 17A) is attached to the monitor (not shown) via a cable 312. Although a separate wriststrap monitor terminal is shown in this embodiment, the wriststrap monitor terminal may also be integrated into the monitor. A wriststrap connector 314 may be connected to a wriststrap cable 316 which is turn removably connected to a wriststrap (not shown.) The terminal 310 may include a piece of magnetic material 320 (shown in FIG. 17B) that provides a mechanical attraction force to disengageably hold the wriststrap connector 314 against the terminal wherein the mechanical attraction force may be overcome by a predetermined amount of force so that the wriststrap connector 314 can be disengaged from the terminal 310. The terminal 310 (shown in FIGS. 17B and 17D) may include one or more non-magnetic/electrical contacts 322 (mounted in this example on a printed circuit board 326 or mounted/placed on any suitable electrical insulator which has no specific magnetic properties of its own) in a recessed area 330 formed by one or more sculpted guide members 328. The terminal may also include a magnetic contact 324. The wriststrap connector 314 may also include a set of contacts 334 as shown in FIG. 17C.

The set of contacts of the wriststrap connector 314 (shown in FIG. 17E) may include a magnetic contact 331 and a set of non-magnetic contacts 333. In accordance with the invention, when the wriststrap connector 314 is placed in close proximity to the terminal 310, the wriststrap connector 314 is attracted via magnetic force between the magnet 320 inside the terminal 310 and the magnetic contact 331 of the wriststrap connector. The sculptured shape of the front panel of the terminal (due to the sculpted guides 328 and the recessed area 330) and the shape of the wriststrap connector 314 (that fits into the recessed area of the terminal) assures correct and stable mutual positioning of the wriststrap connector and its contacts with the set of contacts of the terminal.

The wriststrap connector 314 non-magnetic terminals 333 are positioned in such way that the magnetic contact 331 is slightly recessed relative to the non-magnetic connectors (shown in FIG. 17C) so that a gap 340 (shown in FIG. 17G) is formed when the wriststrap connector 314 mates with the terminal contacts. This gap ensures that a pull force (between the magnetic contact 331 and the magnetic contact 324) is generated that pulls the contacts 333 against the contact 322 to ensure a good electrical connection between the terminal and the wriststrap connector. FIG. 17F illustrates when the wriststrap connector 314 is mated to the terminal 310.

In order to provide the wriststrap monitor (not shown) with information that the wriststrap connector is properly mated to the terminal, the connector 314 has more than two connections (in the example shown in FIGS. 17A-H, the connector has three contacts) and in the wriststrap connector has two contacts 350 (that may be the contacts 333 shown in FIG. 17E) that are electrically connected together so that when it is mated, the electrical circuit in the wriststrap monitor (in a manner well known by those skilled in the art) can verify that the connector and the terminal are properly mated.

FIGS. 18A and 18B illustrate yet another embodiment of the magnetic connector 314 for a wriststrap monitor in accordance with the invention. In this embodiment, the terminal 310 (or the monitor if the terminal is integrated into the monitor) has a different mechanism for verifying the mating status of the terminal 310 and the connector 314. In this embodiment, the terminal 310 may include a light detector 62 (such as a well known light sensitive diode or photodetector in this example) mounted adjacent an opening 360 so that ambient light will reach the light detector via the opening 60 in the front panel when the connector 314 is not mated to the terminal 310. However, when the wriststrap connector 314 is mated, the connector 314 blocks the ambient light which is detected by the light detector (that generates a signal which can be interpreted as indicating that mating has occurred) and the monitor is able to verify the mating of the terminal 310 and the connector 314. In this embodiment, the connector 314 does not need to have three contacts so that a connector 314 with two contacts (one magnetic contact and one electrical contact) may be used.

Figure 19B:
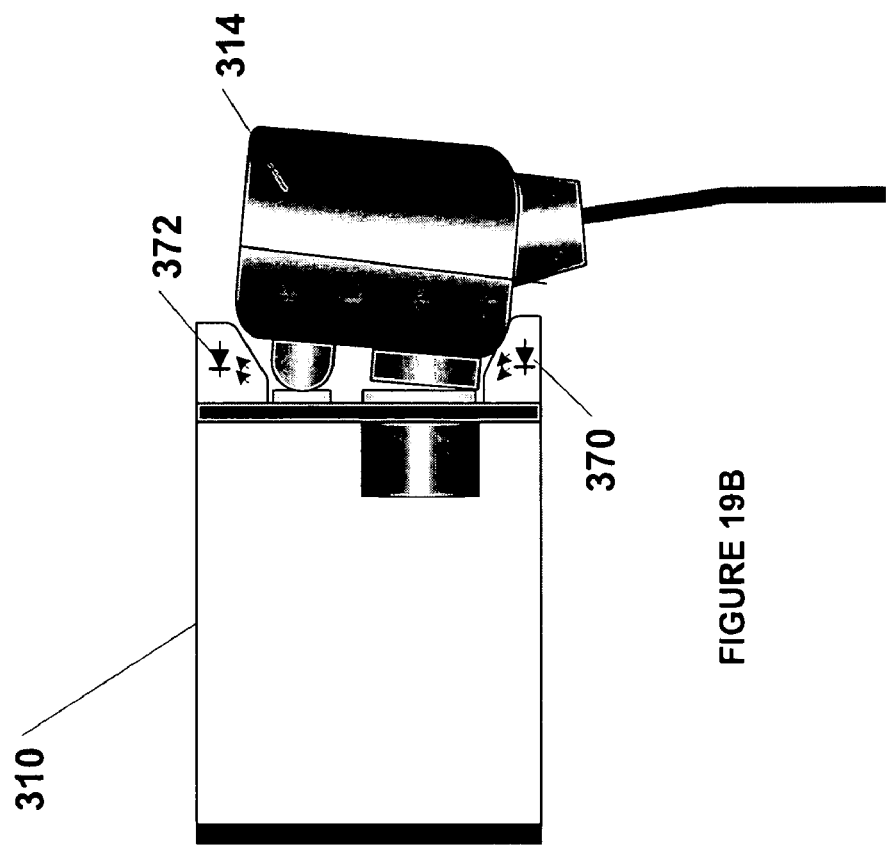
FIGS. 19A and 19B illustrate yet another embodiment of the magnetic connector for a wriststrap monitor in accordance with the invention.
Figure 19A:
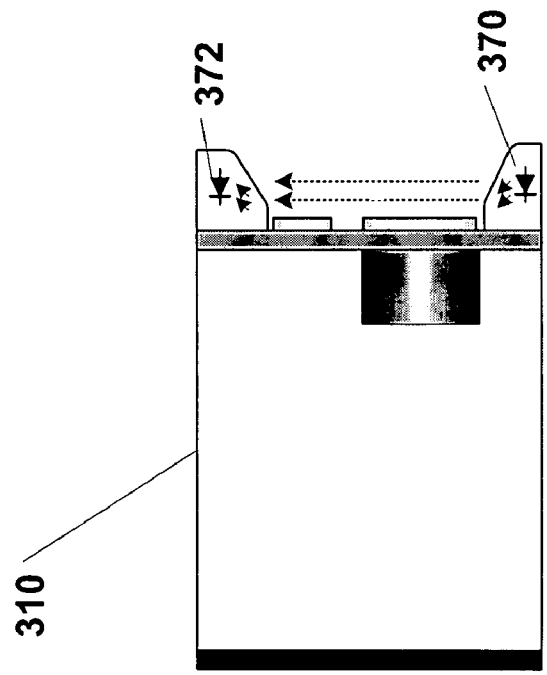

FIGS. 19A and 19B illustrate yet another embodiment of the magnetic connector 314 for a wriststrap monitor in accordance with the invention. In this embodiment, the terminal 310 (or the monitor if the terminal is integrated into the monitor) has a different mechanism for verifying the mating status of the terminal 310 and the connector 314. In this embodiment, the terminal 310 may include a light source 370, such as an LED, and a light detector 372, such as a photodetector, positioned (such as shown in the examples in FIGS. 19A and 19B) so that the wriststrap connector 314 when mated (shown in FIG. 19B) blocks the light path between the light source and the light detector and the light detector generates a signal (or the lack of a signal) that can be interpreted as indicating that the proper mating has occurred. In this embodiment, the connector 314 does not need to have three contacts so that a connector 314 with two contacts (one magnetic contact and one or more electrical contacts) may be used.

FIGS. 20A-20C illustrates yet another embodiment of the magnetic connector 314 for a wriststrap monitor in accordance with the invention. In this embodiment, the terminal 310 has a set of electrical connectors 380 in addition to the magnetic element 320 and the wriststrap connector 314 has a magnetic element 382, which is preferably (but not necessarily) made of soft magnetic material, and a set of electrical non-magnetic contacts 384. In a preferred implementation, the non-magnetic contacts are located on opposite ends of a member and the magnetic contact 382 is located at or near the center of that member. When the mating between the connector 314 and the terminal 301 occurs, the magnetic element 320 and the magnetic element 382 provide a mechanical (magnetic attractive) force that holds the connector 314 and the terminal 310 in place and assures electrical contact between contacts 380 and 384. As shown in FIG. 20C, the magnetic element 382 of the connector 314 and the magnetic element 320 of the terminal unit 310 are releasably coupled to each other when the connector and terminal unit are mated. However, the non-magnetic contacts 384 can slide within the terminal unit so that the connector 314 can rotate while mated without accidental disconnect of the connector 314 as the operator moves around.

FIG. 21 illustrates yet another embodiment of the magnetic connector 314 for a wriststrap monitor in accordance with the invention which is a slight variation of the connector 314 shown in FIGS. 20A-20C. In this embodiment, the terminal set of electrical contacts 100 may be split into two pieces in order to provide some mechanism to verify the mating of the connector 314 and the terminal 310. When the wriststrap connector 314 mates with the terminal 310, the set of contacts 110 provide a electrical connection between split contacts 100 so that the monitor receives an indication of the proper mating of the connector 314 and the terminal 310.

FIGS. 22A-22D illustrate yet another embodiment of the magnetic connector 314 for a wriststrap monitor in accordance with the invention. FIG. 22A illustrates side view of the terminal unit 110 and the connector 314, FIG. 22B is a front view of the terminal and connector, FIG. 22C is a top view of the terminal unit 110 and FIG. 22D is a perspective view of the terminal unit 110. The connector 314 of this embodiment has magnetic element 382 and the non-magnetic elements 384 that have the configuration shown in FIG. 20C wherein the non-magnetic elements 384 are positioned at opposite ends of a member extending out from the magnetic element 382 which is located near or at the center of the member. In this embodiment, the terminal unit 110 has a specially shaped terminal 110 shown in FIGS. 22C and 22D (with a set of electrical contacts 112) with one or more ridge portions 113 and one or more valley portions 114 that cause the wriststrap connector 314 to automatically rotate into a position for proper mating. In particular, when the non-magnetic elements 384 are placed on or near the ridge portions 113 (in an incorrect mating position), the magnetic force of the magnet element 320 will pull the magnetic element 382 towards the magnetic element 320 which causes the non-magnetic elements 384 to slide down the ridge portion 113 into the valley portion 114 which in turn causes the connector 314 to rotate and then properly mate with the terminal unit.

FIGS. 23A and 23B illustrate an embodiment of a magnetic connector 140 in accordance with the invention. This embodiment may be used for a wriststrap (as the embodiments described above), but it can also be used for other connections in which it is desirable to have a disengagable connection. The connector 140 (that has an metallic portion that is inserted into the receptacle) mates with a receptacle 144 that has an opening 146, a first magnetic element 148 and a second magnetic element 150 which is suspended on a spring suspension member 152 (in this example it is cantilevered, but can be of any spring-loaded construction). This embodiment may include other connectors and/or each magnet may also be an electrical connector, though it is entirely possible to have electrical connector mechanically attached to the magnet which wouldn't be electrical connector by itself. When the connector 140 is inserted into the receptacle 144, the connector 140 is attracted by the magnetic element 148 and then the second magnetic element 150 is attracted to the connector 140 and makes an electrical connection to the connector 140 as shown in FIG. 23B. Using this connector, there is no friction force nor any spring-loaded force which, over time, wears down the connector 140 resulting in a failure of the connector. The spring member 152 does not need to be strong to assure electrical connection as the magnetic member 150 assures a good electrical connection. A variation of the connector 140 is that the spring loaded magnet 150 can be released when the connector 140 is pulled away from the magnet element 148 to completely eliminate any friction. As above, this connector may include a mechanism (electrical or light based as described above) to verify the proper mating of the connector with the receptacle.

Figure 24:
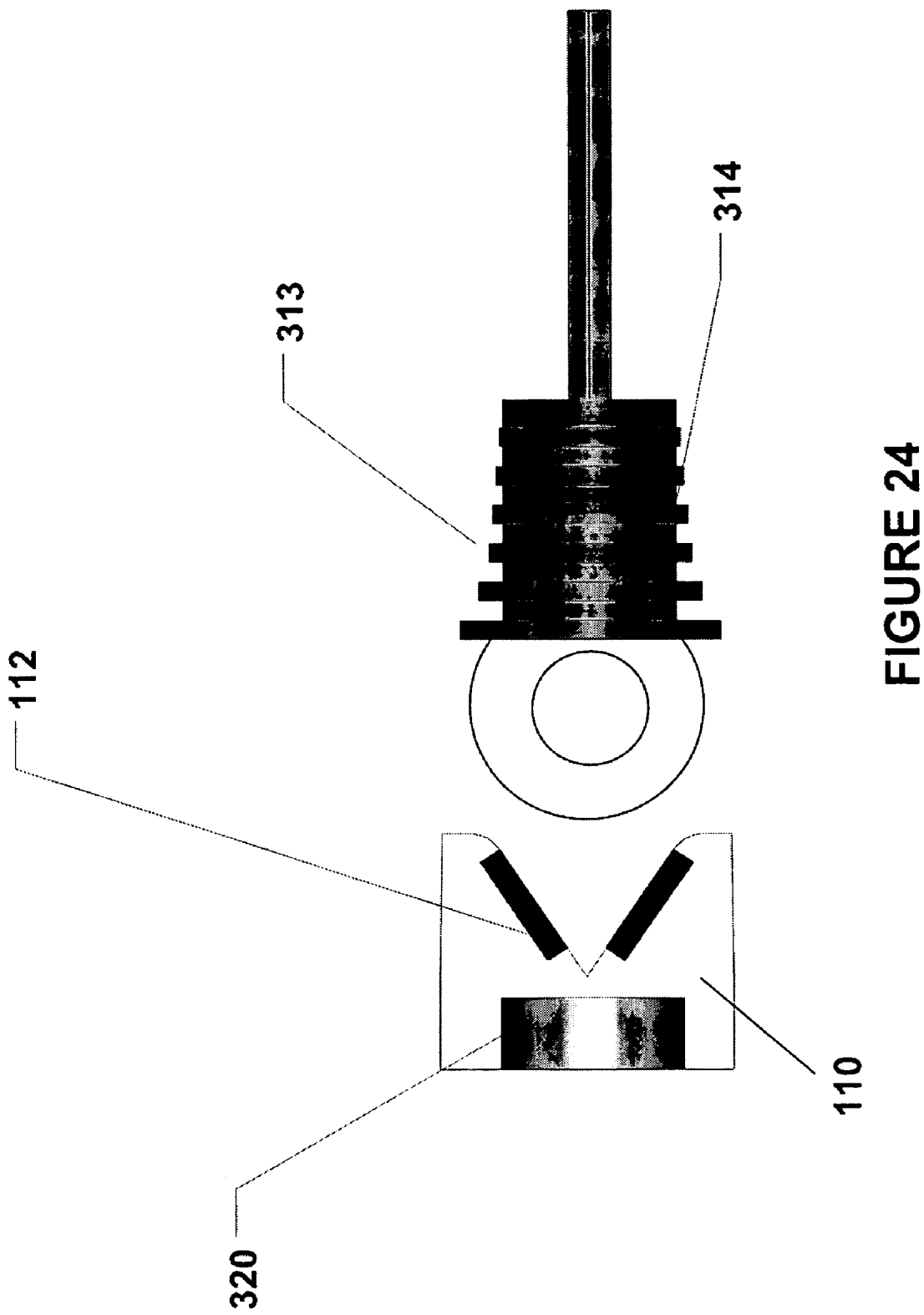
FIG. 24 illustrates the magnetic connector with a cushion in accordance with the invention.

FIG. 24 illustrates the connector 314 having a cushion member 313, such as a plastic material or any other suitable material and having any suitable shape, located adjacent to the magnetic member of the connector. The example in FIG. 14 is the terminal unit 110 and connector 314 shown in FIG. 22B. However, the cushion member may be incorporated into any of the magnetic connectors described in this application. The cushion member 313 provides a cushion between the magnetic contact of the connector (which is hard) and the user of the wriststrap should the connector become disengaged from the terminal unit. Thus, if the connected disengages from the terminal unit, the connector may recoil and hit the rear of the user and the cushion member reduces the impact when the connector hits the user.

While the foregoing has been with reference to a particular embodiment of the invention, it will be appreciated by those skilled in the art that changes in this embodiment may be made without departing from the principles and spirit of the invention, the scope of which is defined by the appended claims.

What is claimed is:

1. A wriststrap connector, comprising:
   a wriststrap cord connected to a wriststrap;
   one or more non-magnetic contacts that can be coupled to a terminal of a wriststrap monitor device; and
   a magnetic contact that can be magnetically coupled to the terminal of the wriststrap monitor device wherein the wriststrap connector is disengagably coupled to the terminal of the wriststrap monitor device by the magnetic contact.

2. The connector of claim 1, wherein the one or more non-magnetic contacts further comprises two contacts connected to each other that, when the connector is mated to the terminal, completes an electrical circuit to generate an indication of the proper mating of the connector with the terminal.

3. The connector of claim 1, wherein the magnetic contact is offset from the one or more non-magnetic contacts that forms a gap when the connector is mated to the terminal, the gap creating a pull magnetic force that ensures that the one or more non-magnetic contacts make a good electrical contact with the terminal.

4. The connector of claim 1, wherein the one or more non-magnetic contacts are positioned at opposite ends of a member and the magnetic contact is positioned in the middle of the member so that the non-magnetic contacts may rotate relative to a terminal while the magnetic contact remains mated to a magnetic element of the terminal.

5. The connector of claim 1, wherein the one or more non-magnetic contacts are positioned at opposite ends of a member and the magnetic contact is positioned in the middle of the member so that the member is able to slide down a ridge portion of a terminal unit in order to properly mate the connector with the terminal unit.

6. The connector of claim 1 further comprising a cushion member adjacent to the magnetic contact that protects a user when connector recoils when disengaged by force from a terminal unit.

7. A wriststrap connector and monitor system, the system comprising:
   a wriststrap connector having a wriststrap cord connected to a wriststrap, one or more non-magnetic contacts that can be coupled to a terminal of a wriststrap monitor device and a magnetic contact that can be magnetically coupled to the terminal of the wriststrap monitor device wherein the wriststrap connector is disengagably coupled to the terminal of the wriststrap monitor device by the magnetic contact;
   a terminal unit having a magnetic element that magnetically attracts the magnetic contact of the connector so that the connector is magnetically disengagably coupled to the terminal unit.

8. The system of claim 7, wherein the one or more non-magnetic contacts further comprises two contacts connected to each other that, when the connector is mated to the terminal unit, completes an electrical circuit to generate an indication of the proper mating of the connector with the terminal unit.

9. The system of claim 7, wherein the magnetic contact is offset from the one or more non-magnetic contacts that forms a gap when the connected is mated to the terminal, the gap creating a pull magnetic force that ensures that the one or more non-magnetic contacts make a good electrical contact with the terminal unit.

10. The system of claim 7, wherein the one or more non-magnetic contacts of the connector are positioned at opposite ends of a member and the magnetic contact of the connector is positioned in the middle of the member so that the non-magnetic contacts of the connector may rotate relative to a terminal unit while the magnetic contact of the connector remains mated to the magnetic element of the terminal unit.

11. The system of claim 7, wherein the terminal unit further comprises one or more non-magnetic contacts that couple to the one or more non-magnetic contacts of the wriststrap connector when the wriststrap connector is mated with the terminal unit and a magnetic contact adjacent the magnetic element that couple to the magnetic contact of the wriststrap connector when the wriststrap connector is mated with the terminal unit.

12. The system of claim 11, wherein the one or more non-magnetic contacts of the terminal unit further comprises two non-magnetic contacts connected to each other that, when the connector is mated to the terminal unit, completes an electrical circuit to generate an indication of the proper mating of the connector with the terminal unit.

13. The system of claim 7, wherein the terminal unit further comprises a mating indication circuit that indicates that the wriststrap connector and terminal unit are properly mated with each other.

14. The system of claim 13, wherein the mating indication circuit further comprises a light detector that detects ambient light that is blocked when the wriststrap connector is properly mated to the terminal unit to indicate proper mating of the wriststrap connector and the terminal unit.

15. The system of claim 13, wherein the mating indication circuit further comprises a light source and a light detector wherein the light path between the light source and the light detector is blocked when the wriststrap connector is properly mated to the terminal unit to indicate proper mating of the wriststrap connector and the terminal unit.

16. The system of claim 7, wherein the terminal unit further comprises one or more guide portions adjacent to a recessed area wherein the wriststrap connector is guided into proper mating with the terminal unit.

17. The system of claim 7 further comprising a wriststrap monitor wherein the terminal unit is integrated into the wriststrap monitor.

18. The system of claim 7, wherein the one or more non-magnetic contacts of the wriststrap connector are positioned at opposite ends of a member and the magnetic contact is positioned in the middle of the member and wherein the terminal unit further comprises one or more ridge portions and one or more valley portions wherein the member of the wriststrap connector slides down the ridge portions into the valley portions for proper mating of the wriststrap connector with the terminal unit due to the magnetic attractive force of the magnetic element of the terminal unit.

19. The system of claim 7, wherein the connector further comprises a cushion member adjacent to the magnetic contact that protects a user when connector recoils when disengaged by force from a terminal unit.

20. A magnetic connector system, comprising:
a connector having a metallic portion; and
a unit having a receptacle into which the metallic portion is inserted when mating the connector to the unit, the receptacle further comprising a first magnetic element that attracts the metallic portion when the connector is mated with the receptacle, a bias member and a second magnetic element biased away from the metallic portion by the bias member wherein the second magnetic element establishes an electrical connection with the metallic portion as the second magnetic element is attracted to the metallic portion.

21. The system of claim 20, wherein the first magnetic element further comprises a magnet and the second magnetic element further comprises a magnet.

22. The system of claim 20, wherein the bias member further comprises a spring.

23. The system of claim 22, wherein the spring further comprises a cantilever spring member.

24. The system of claim 20, wherein the unit further comprises a mating indication circuit that indicates that the connector and unit are properly mated with each other.

25. The system of claim 24, wherein the mating indication circuit further comprises a light detector that detects ambient light that is blocked when the connector is properly mated to the unit to indicate proper mating of the connector and the unit.

26. The system of claim 24, wherein the mating indication circuit further comprises a light source and a light detector wherein the light path between the light source and the light detector is blocked when the connector is properly mated to the unit to indicate proper mating of the connector and the unit.

27. The system of claim 20, wherein the connector further comprises a wriststrap connector having a wriststrap cord wherein the wriststrap connector disengagably couples the wriststrap connector to the unit.

28. The system of claim 20, wherein the connector further comprises a cushion member adjacent to the metallic portion that protects a user when connector recoils when disengaged by force from the unit.

* * * * *

UNITED STATES PATENT AND TRADEMARK OFFICE
CERTIFICATE OF CORRECTION

PATENT NO. : 7,539,002 B1  Page 1 of 1
APPLICATION NO. : 11/497160
DATED : May 26, 2009
INVENTOR(S) : Vladimir Kraz It is certified that error appears in the above-identified patent and that said Letters Patent is hereby corrected as shown below:

Column 4,
Line 28, delete "22'" and insert --22-- therefor.

Column 5,
Line 63, delete "2$d$'" and insert --2$d$-- therefor.

Column 8,
Line 40, delete "152'" and insert --152-- therefor.

Column 17,
Line 3, Claim 9, delete "connected" and insert --connector-- therefor.

Signed and Sealed this

Tenth Day of November, 2009

David J. Kappos
*Director of the United States Patent and Trademark Office*